US009005658B2

(12) United States Patent
Schlutermann et al.

(10) Patent No.: US 9,005,658 B2
(45) Date of Patent: Apr. 14, 2015

(54) ORAL PREPARATION WITH CONTROLLED RELEASE

(75) Inventors: Burkhard Schlutermann, Au (DE); Manfred Kohlmeyer, Basel (CH)

(73) Assignee: ADD Advanced Drug Delivery Technologies Ltd., Reinach (CH)

( * ) Notice: Subject to any disclaimer, the term of this patent is extended or adjusted under 35 U.S.C. 154(b) by 1620 days.

(21) Appl. No.: 12/086,827

(22) PCT Filed: Dec. 15, 2006

(86) PCT No.: PCT/EP2006/012134
§ 371 (c)(1),
(2), (4) Date: Jul. 22, 2009

(87) PCT Pub. No.: WO2007/073894
PCT Pub. Date: Jul. 5, 2007

(65) Prior Publication Data
US 2009/0311319 A1      Dec. 17, 2009

(30) Foreign Application Priority Data

Dec. 16, 2005   (DE) .......................... 10 2005 060 393

(51) Int. Cl.
  *A61K 31/138*    (2006.01)
  *A61K 9/20*      (2006.01)
  *A61K 9/16*      (2006.01)
  *A61K 9/50*      (2006.01)

(52) U.S. Cl.
  CPC ............. *A61K 9/5078* (2013.01); *A61K 9/2081* (2013.01)

(58) Field of Classification Search
  USPC ........................................................ 424/464
  See application file for complete search history.

(56) References Cited

U.S. PATENT DOCUMENTS

| 5,508,276 | A  | * | 4/1996  | Anderson et al. ............. 514/183 |
| 5,843,479 | A  | * | 12/1998 | Kelm et al. .................... 424/479 |
| 6,605,303 | B1 | * | 8/2003  | Karehill et al. ............... 424/484 |
| 2003/0185887 | A1 | | 10/2003 | Chen |
| 2005/0008701 | A1 | | 1/2005  | Sriwongjanya |

FOREIGN PATENT DOCUMENTS

| EP | 0 220 143 A1 | 4/1987 |
| EP | 1 477 163 A | 11/2004 |
| WO | WO93/15725 A | 8/1993 |
| WO | WO2005/084636 A | 9/2005 |
| WO | WO2005/084636 A2 * | 9/2005 | .................. 424/464 |
| WO | WO2005084636 A2 * | 9/2005 | .................. 424/464 |
| WO | WO2005/099671 A | 10/2005 |

OTHER PUBLICATIONS

PCT Search Report dated Jun. 18, 2007.

* cited by examiner

*Primary Examiner* — Audrea Buckley
(74) *Attorney, Agent, or Firm* — Frommer Lawrence & Haug LLP

(57) ABSTRACT

A pharmaceutical pellet is provided, comprising a spherical core containing the active substance with a smooth surface and a coating on the core, which controls pH-independent release of the active substance. With a pellet of this kind, the release of the active substance may follow a profile with a lag-phase from 60 minutes to 840 minutes, where during the lag-phase a proportion of 5 wt. % or less of the active substance is released. Furthermore, the active substance may be released from the pellet with a profile such that, after the lag-phase, the release of the active substance is between 3 and 25 wt. % per hour. The active substance is a metoprolol salt.

21 Claims, 25 Drawing Sheets

ORAL PREPARATION WITH CONTROLLED RELEASE

FIELD OF THE INVENTION

The present invention relates to new pharmaceutical pellets, multiparticulate dosage forms based on said pellets, methods of production of pellets and methods of production of dosage forms using the pellets. The pellets and the multiparticulate dosage forms based on the pellets are characterized in particular by controlled release of the active substance. The pellets comprise a salt of metoprolol, such as, for example, metoprolol succinate, as active substance.

BACKGROUND OF THE INVENTION

When medicinal products are administered orally, the active substance is released in the gastrointestinal tract, and a proportion of the active substance is absorbed. By controlling the release of the active substance it is possible to influence the extent of absorption and the duration of action. Accordingly, various proposals have been made for controlling the release of the active substance by suitable galenical formulation of the active substance.

One approach is to provide dosage forms with coatings, so that the release of the active substance can be influenced in relation to the solubility or permeability of the coatings. Said coatings can for example be applied to tablets or capsules. In this case, however, there is the disadvantage that if the coating is defective or damaged, the release of the total dose of active substance may not be controlled in the desired manner.

An alternative is offered by multiparticulate dosage forms, in which the total amount of the active substance is distributed over a larger number of smaller units, such as pellets. If the individual pellets are provided with coatings, in the case of a defective coating on one pellet only a correspondingly small proportion of the total dose of active substance is not released in the desired manner.

A further advantage of these dosage forms based on pellets is that, after ingestion, sufficiently small pellets pass relatively quickly from the stomach into the intestine. In contrast, unless they disintegrate, tablets may remain in the stomach for quite a long time, and moreover the length of time varies considerably.

Despite the known advantages of pellets or multiparticulate dosage forms it is, however, difficult to obtain a desired release behavior. This is associated with the fact that, in the state of the art, it is difficult to prepare uniformly coated pellets. Even the pellet cores that are to be coated are of inadequate quality. In particular, pellets produced by extrusion are often of nonuniform shape and moreover have a rough and uneven surface, so that subsequent coating with film becomes difficult and it is scarcely possible to obtain films of good quality.

The films or coatings employed for controlling release can have various compositions. Thus, proposals have been made for controlling release in relation to pH value, time or bacterial enzymes that are present in the intestine.

With pH-controlled systems, however, there is the problem that the release of the active substance is altered by food intake, which has an effect on the pH value in the gastrointestinal tract. Moreover, there are considerable differences regarding pH values in the gastrointestinal tract between different individuals. Variability has also been reported in the case of controlled-release dosage forms controlled enzymatically.

Certain controlled-release dosage forms are therefore not completely satisfactory. There is the further problem that it is not possible to produce desired (specified) release profiles. Furthermore, the production of controlled-release dosage forms is often difficult. There is therefore a need for new controlled-release dosage forms as well as new methods for the production of controlled-release dosage forms.

The observations above apply in particular to dosage forms which contain a metoprolol salt, such as metoprolol succinate, for example. Metoprolol and its salts are cardio-selective beta blockers. They are used in the treatment of hypertension and also of a series of cardiovascular disorders. With disorders of this kind, a constant level of active substance in the blood is especially desirable. It is advantageous, furthermore, if preparations are made available that are suitable for a once-daily dosage. In this context a variety of dosage forms have been developed. They include tablets in which metoprolol is embedded in an insoluble matrix. In another preparation, coatings are applied to insoluble silicon dioxide cores. In terms of application and/or production, however, the stated dosage forms are not entirely satisfactory.

OBJECTS AND BRIEF DESCRIPTION OF THE INVENTION

One object of the present invention is to provide a pharmaceutical pellet for which the release of the active substance can be controlled independently of the pH value and independently of the action of enzymes, metoprolol in the form of a salt, for example metoprolol succinate, being present as active substance.

Another object is to provide a pharmaceutical pellet for which the release of the active substance follows a profile with a lag-phase. A further object is to provide a pellet for which the release of the active substance takes place at an established rate after a lag-phase. Furthermore, according to the invention, pellet products or collections of pellets are to be provided which comprise a multiplicity of individual pellets, each satisfying the specified requirements. Finally, according to the invention, methods are to be provided for the production of pellets, pellet products and other dosage forms. The common factor among all the pellets, pellet products and dosage forms mentioned is that metoprolol in the form of a salt, for example metoprolol succinate, is present as active substance.

Now, according to the invention, it has been found that preparations can be provided for which the release of the active substance takes place independently of pH and independently of enzymes, if pellets are used that have a spherical core containing the active substance with a smooth surface and a coating on the core, metoprolol in the form of a salt, for example metoprolol succinate, being present as active substance.

Preparations having a practically linear release profile of the active substance may in particular be provided. The formulations are ideally suitable for administration once a day.

BRIEF DESCRIPTION OF THE FIGURES

The invention is explained in more detail below, referring to the figures.

is plotted versus time (minutes). The percentage amount of coating material (polyvinyl acetate, triethyl citrate and talc in the composition stated above) relative to the weight of the pellet cores containing the active substance, for the individual batches, is given as a measure for the thickness of the coating.

Figure 2:
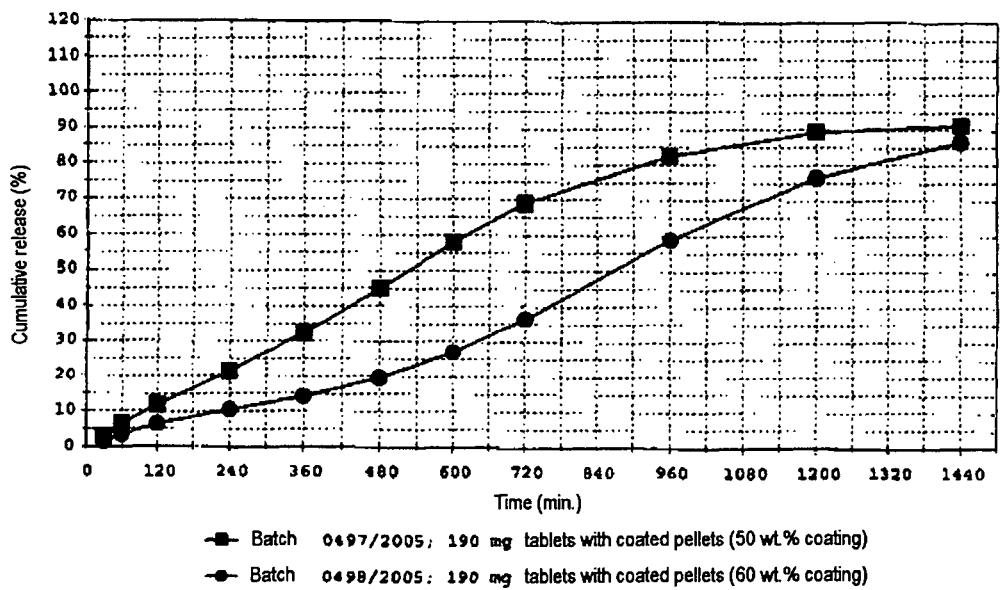

FIG. 2 shows the release of the active substance from film tablets with a dimension of 16.5 mm*9 and a weight of 692.0 mg, which contain 190 mg metoprolol succinate. The tablets were produced in each case using pellets that have a pellet core with the active substance metoprolol succinate. In one case, the pellet core was coated with 50 wt. % of a coating consisting, relative to the weight of the pellet cores, of polyvinyl acetate, triethyl citrate (10 wt. %, relative to the weight of the polyvinyl acetate) and talc (10 wt. %, relative to the weight of the polyvinyl acetate) and in the other case 60 wt. % of the same coating. In each case a protective coating of hydroxypropyl methylcellulose and colloidal silica was applied on top. The cumulative release (%), plotted versus time, is shown. The curves show inter alia how the amount of coating which was applied to the pellet core affects the release.

Figure 3:
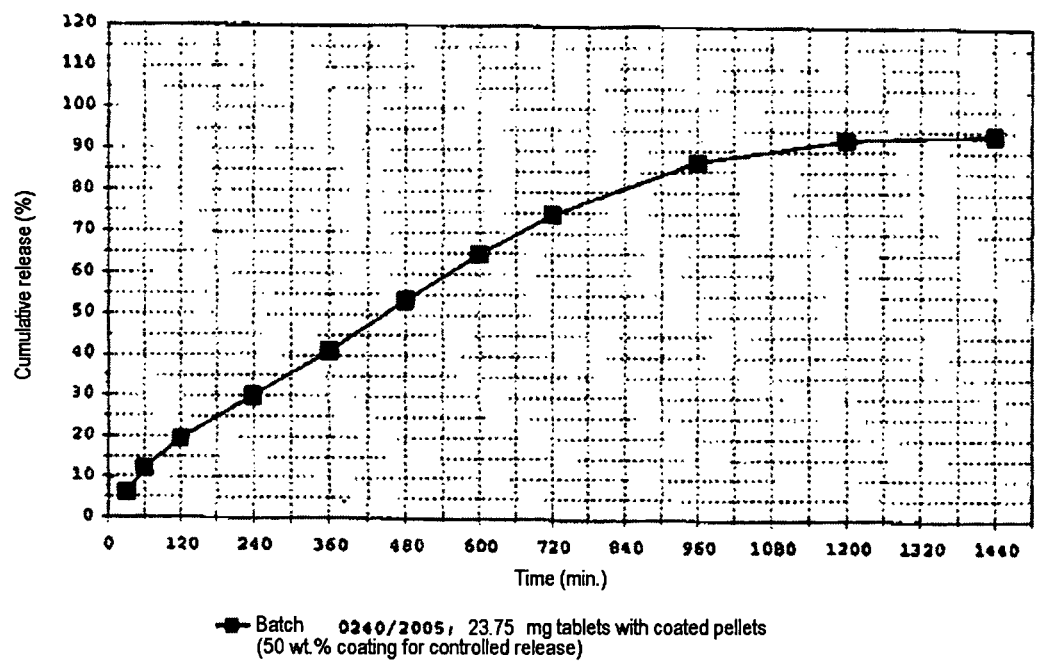

FIG. 3 shows the release of the active substance from tablets with a diameter of 6 mm, a tablet core weight of approximately 84 mg, containing 23.75 mg metoprolol succinate. The tablets were produced in each case using pellets that have a pellet core with the active substance metoprolol succinate. The pellet core was coated with 50 wt. % of a coating consisting, relative to the weight of the pellet cores, of polyvinyl acetate, triethyl citrate (10 wt. %, relative to the weight of the polyvinyl acetate) and talc (10 wt. %, relative to the weight of the polyvinyl acetate) and a protective coating of hydroxypropyl methylcellulose and colloidal silica. The cumulative release (%) plotted versus time is shown.

Figure 4:
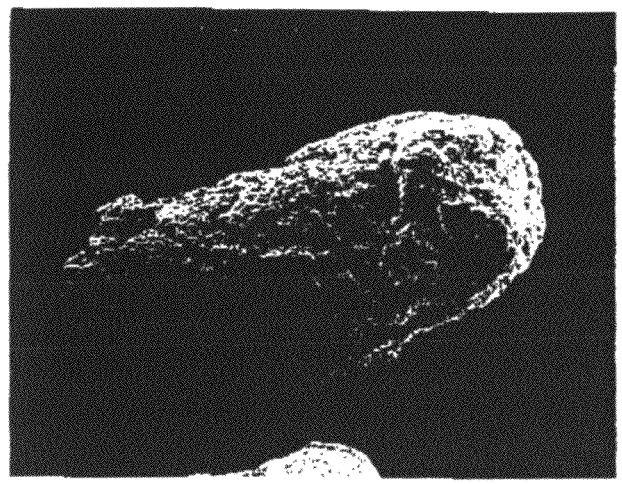

FIG. 4 shows a scanning electron micrograph (50-times magnification) of an extruded pellet with irregular shape and a rough surface.

Figure 5:
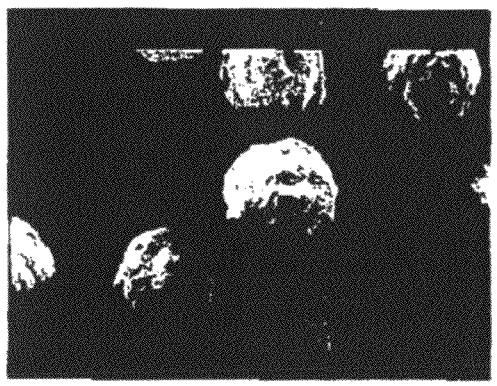

FIG. 5 shows an electron micrograph (25-times magnification) of pellets with the batch designation SFD E 0724, which do not fulfill the criteria according to the invention for a pellet core with a smooth surface.

FIG. 6 presents data obtained using a laser profilometer, characterizing the surface of a pellet with the batch designation SFD E 0724. FIG. 6A is a graphical representation of the measurement results as a surface graph. FIG. 6B shows the measurement results as a contour diagram. FIG. 6C shows a surface graph based on a reduced data set. FIG. 6D shows the corresponding contour diagram. FIG. 6E shows the deviations of the measured points of the reduced data set from the ideal surface determined by the method of least squares.

FIG. 7 presents data obtained using a laser profilometer, characterizing the surface of another pellet with the batch designation SFD E 0724. FIG. 7A is a graphical representation of the measurement results as a surface graph. FIG. 7B shows the measurement results as a contour diagram. FIG. 7C shows a surface graph based on a reduced data set. FIG. 7D shows the corresponding contour diagram. FIG. 7E shows the deviations of the measured points of the reduced data set from the ideal surface determined by the method of least squares.

Figure 8:
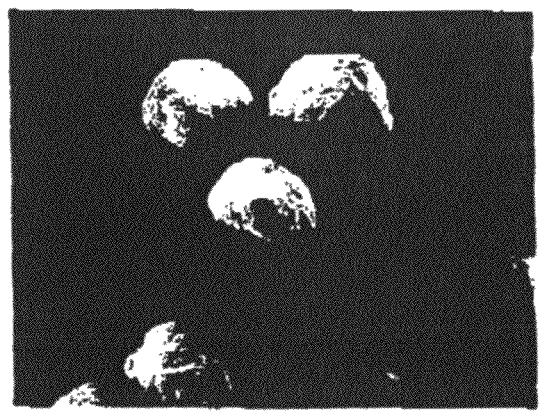

FIG. 8 shows an electron micrograph (25-times magnification) of pellets with the batch designation SFD E 0718, which do not fulfill the criteria according to the invention for a pellet core with a smooth surface.

FIG. 9 presents data obtained using a laser profilometer, characterizing the surface of a pellet with the batch designation SFD E 0718. FIG. 9A is a graphical representation of the measurement results as a surface graph. FIG. 9B shows the measurement results as a contour diagram. FIG. 9C shows a surface graph based on a reduced data set. FIG. 9D shows the corresponding contour diagram. FIG. 9E shows the deviations of the measured points of the reduced data set from the ideal surface determined by the method of least squares.

FIG. 10 presents data obtained using a laser profilometer, characterizing the surface of another pellet with the batch designation SFD E 0718. FIG. 10A is a graphical representation of the measurement results as a surface graph. FIG. 10B shows the measurement results as a contour diagram. FIG. 10C shows a surface graph based on a reduced data set. FIG. 10D shows the corresponding contour diagram. FIG. 10E shows the deviations of the measured points of the reduced data set from the ideal surface determined by the method of least squares.

Figure 11:

FIG. 11 shows an electron micrograph (25-times magnification) of pellets with the batch designation SFD E 0572, which do not fulfill the criteria according to the invention for a pellet core with a smooth surface.

FIG. 12 presents data obtained using a laser profilometer, characterizing the surface of a pellet with the batch designation SFD E 0572. FIG. 12A is a graphical representation of the measurement results as a surface graph. FIG. 12B shows the measurement results as a contour diagram. FIG. 12C shows a surface graph based on a reduced data set. FIG. 12D shows the corresponding contour diagram. FIG. 12E shows the deviations of the measured points of the reduced data set from the ideal surface determined by the method of least squares.

Figure 13:
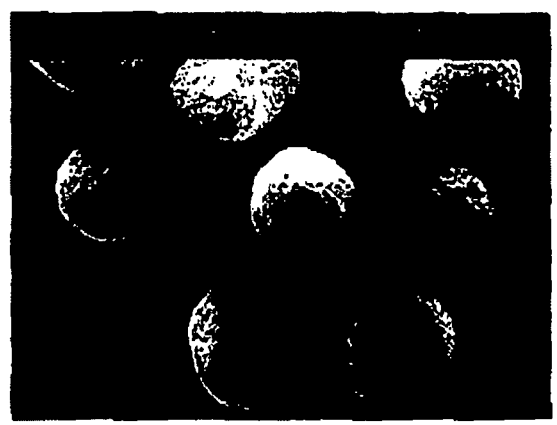

FIG. 13 shows an electron micrograph (25-times magnification) of pellets with the batch designation SFD E 0614, which do not fulfill the criteria according to the invention for a pellet core with a smooth surface.

FIG. 14 presents data obtained using a laser profilometer, characterizing the surface of a pellet with the batch designation SFD E 0614. FIG. 14A is a graphical representation of the measurement results as a surface graph. FIG. 14B shows the measurement results as a contour diagram. FIG. 14C shows a surface graph based on a reduced data set. FIG. 14D shows the corresponding contour diagram. FIG. 14E shows the deviations of the measured points of the reduced data set from the ideal surface determined by the method of least squares.

FIG. 15 presents data obtained using a laser profilometer, characterizing the surface of another pellet with the batch designation SFD E 0614. FIG. 15A is a graphical representation of the measurement results as a surface graph. FIG. 15B shows the measurement results as a contour diagram. FIG. 15C shows a surface graph based on a reduced data set. FIG. 15D shows the corresponding contour diagram. FIG. 15E shows the deviations of the measured points of the reduced data set from the ideal surface determined by the method of least squares.

Figure 16:
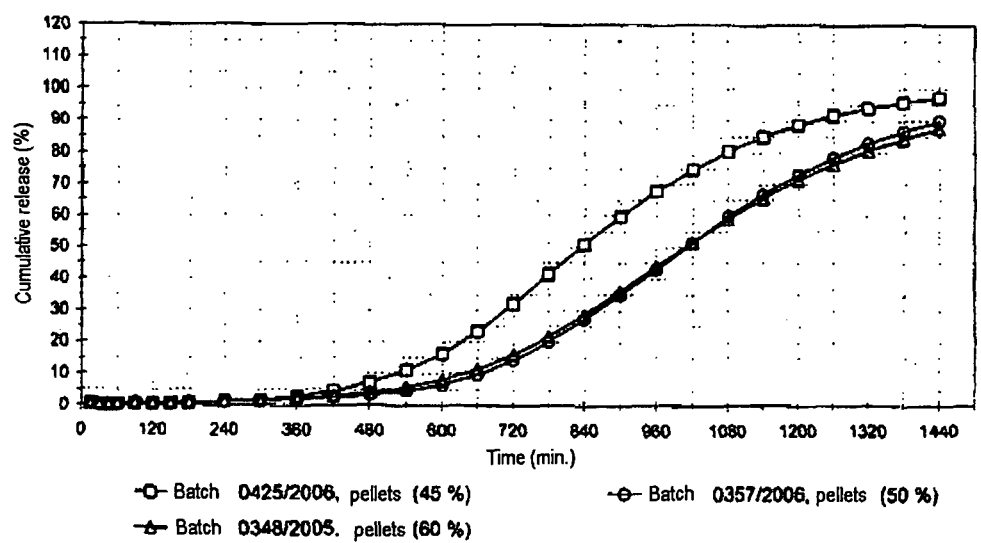

FIG. 16 shows the influence of the thickness of the release-controlling coating on the release of the active substance in the case of pellets containing the active substance metoprolol succinate. The cumulative release (%) is plotted versus time (minutes). The percentage amount of coating material (polyvinyl acetate, triethyl citrate and talc) relative to the weight of the pellet cores containing the active substance, for the individual batches, is given as a measure for the thickness of the coating.

Figure 17:
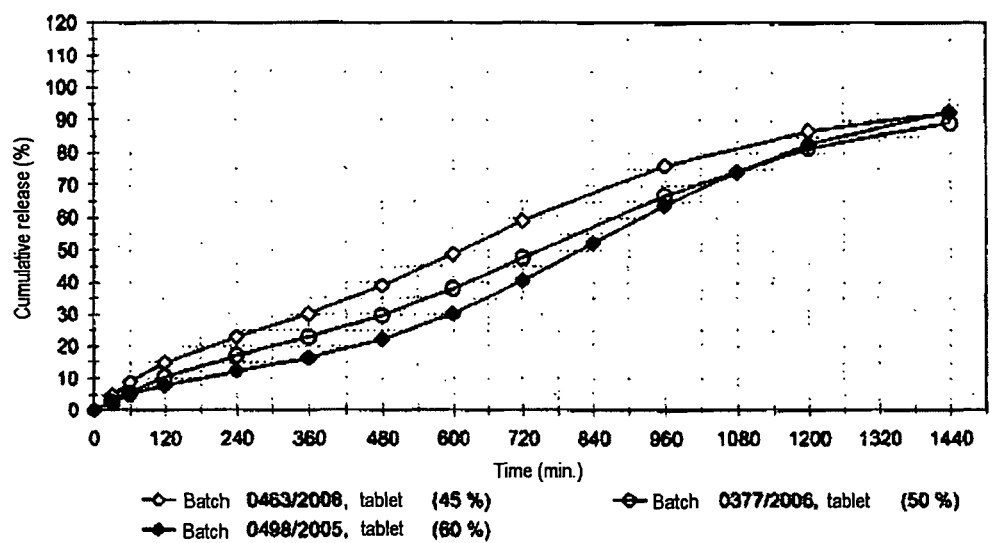

FIG. 17 shows the release of the active substance from tablets containing 190 mg of metoprolol succinate. The tablets were produced in each case using pellets that have a pellet core with the active substance metoprolol succinate. The pellet core was coated in one case with 45 wt. %, 50 wt. % or 60 wt. % of a coating consisting, relative to the weight of the pellet cores, of polyvinyl acetate, triethyl citrate and talc. In each case a protective coating of hydroxypropyl methylcellulose and colloidal silica was applied on top. The cumulative release (%) plotted versus time is shown. The curves show inter alia how the amount of coating which was applied to the pellet core affects the release.

DETAILED DESCRIPTION OF THE INVENTION

Definitions

Some technical terms used in the description and the claims are explained below.

The expression "core" of a pharmaceutical pellet is to be understood here as meaning that the entire inner portion of the pellet is enclosed beneath a coating that controls the pH-independent release of the active substance. The core can be homogeneous or can have an internal structure. Examples include cores where the active substance is distributed homogeneously in a carrier material; cores where the active substance is distributed together with one or more excipients in a carrier material; seed cores coated with a layer of active substance, where the layer of active substance can contain one or more excipients along with the active substance; and cores of the type stated above, which additionally have one or more coatings under the release-controlling coating, for example protective coatings or separating layers of water-soluble excipients, such as water-soluble film-forming agents.

Salts of metoprolol which can be administered orally, can be considered as active substances according to the invention. The hydrochloride salt of metoprolol is known, for example, from DE 21 06 209 B2. The succinate is known from EP 0 293 347 A1. A further known salt is metoprolol tartrate. According to the invention, metoprolol succinate is preferred.

The core of a pharmaceutical pellet typically has a diameter in the range from 0.2 to 2 mm, in particular from 0.3 to 1.6 mm (for example from 0.4 to 1.6 mm) and quite especially from 0.3 to 1.4 mm (for example from 0.4 to 1.4 mm).

A pellet or a core is described as spherical if the length-width ratio (i.e. the ratio of the length (largest dimension) of the pellet or core, divided by the width (smallest dimension), determined at an angle of 90° to the length) is less than about 1.4.

Preferably the length-width ratio of a spherical particle is less than about 1.3, more preferably less than about 1.2, even more preferably less than about 1.1 and in particular less than about 1.05.

According to the invention, the spherical core of the pharmaceutical pellet, which contains the active substance, and typically also the pellet itself have a smooth surface. This means that the surface roughness does not exceed a defined limit. The roughness also describes the deviation of a real surface from an ideal smooth surface.

According to the invention, it proved desirable to scan a suitable segment of the surface of the pellet core or of the pellet, and in particular by optical methods. The results of such scanning can then yield a numerical value for the roughness. More precisely, the surface profile is investigated for a segment of the surface of the pellet core or of the pellet. As far as possible the segment should be selected so that it is representative of the surface of the particle. Thus, measurements are performed on a segment of the surface corresponding to 5 to 50%, in particular 5 to 25%, and especially 5 to 15% of the total surface of the pellet. For this surface segment, measurement points are established that correspond to a grid. Points of the grid are typically between 2.5 and 50 µm, in particular between 12.5 and 50 µm apart. The number of measurement points is typically in the range from 50 to 5000.

The data obtained are then compared with an ideal surface. For this it is assumed that the surface region being measured can be represented by a segment of a spherical surface. This idealized spherical surface can be determined mathematically by calculating the segment from a spherical surface that is the best fit with the experimentally determined topography. The function that is minimized is the root-mean-square distance of the measured points of the profile from the spherical surface. The free parameters are then the coordinates of the center of the sphere ($x_{0s}$, $y_{0s}$, $z_{0s}$) and the radius of the sphere R. The roughness can then finally be determined from the distances di of the measured points of the profile in the ideal spherical surface. For this, a root-mean-square value $$s_d = \sqrt{\sum_{i=1}^{N} d_i^2} \Big/ \sqrt{N}$$

is determined. In the present application $s_d$ is termed the "mean roughness". For a smooth pellet core or a smooth pellet the mean roughness is typically less than 10 µm and preferably less than 7.5 µm. The relative mean roughness, i.e. the roughness divided by the radius of the sphere R, is preferably less than 2%, in particular less than 1.5% and quite especially preferably less than 1.2%.

Based on the measurements described above, the smoothness of the surface of a core containing an active substance can also be described with additional parameters. One parameter is the maximum deviation, i.e. the maximum absolute distance of a point of the profile from the ideal smooth surface. This value is preferably not more than 40 µm, in particular not more than 30 µm, even more preferably not more than 25 µm and quite especially preferably not more than 20 µm.

For a spherical pellet, it is also possible to state a maximum relative deviation. This means the maximum absolute deviation, divided by the radius of the sphere determined within the scope of optimization. Preferably the maximum relative deviation is not more than 5%, in particular not more than 3%.

A preferred method of determination of the roughness of a pellet will be described later.

pH-independent release of the active substance means that the release of the active substance does not vary significantly when pellets according to the invention are exposed to media with pH values such as are encountered in various segments of the gastrointestinal tract. These pH values range from 1.0 to 8.0.

Methods for determining the release of the active substance are described in the USP (United States Pharmacopeia) and in the Ph.Eur. Reference will be made to these methods here. In particular, a paddle-apparatus is used. The stirring speed is 50 revolutions per minute. The temperature of the test medium is 37° C. A phosphate buffer with a pH value of 6.8 is used as the test medium.

According to one aspect of the invention, release of the active substance takes place with a defined profile. The profile has a lag-phase, and during the lag-phase a proportion of 5 wt. % or less of the active substance is released. The lag-phase lasts 60 to 840 minutes, preferably 60 minutes to 540 minutes.

According to one aspect of the invention, after a lag-phase, at least 80 wt. % of the active substance still remaining is released within 1140 minutes. According to another aspect of the invention, the release of the active substance, after a lag-phase, is between 3 and 25 wt. % per hour, preferably between 3 and 15 wt. % per hour and in particular between 3 and 10.0 wt. % per hour.

Preferred Embodiments—Pellets

Pharmaceutical pellets according to the invention have a core, which contains a salt of metoprolol. Salts with high water solubility are preferred. Metoprolol succinate is particularly preferred.

The core also typically contains one or more binders. Water-soluble binders are preferred. These include calcium carboxymethyl cellulose, polymers based on acrylic acid (Carbopol), gelatin, hydroxyethyl cellulose, hydroxypropyl cellulose, hydroxypropyl methylcellulose, polyethylene glycol (macrogol), methyl cellulose, sodium carboxymethyl cellulose, sodium carboxy-methyl starch, polyoxypropylene-polyoxyethylene block polymers (poloxamers), polyvinyl alcohol, polyvinyl pyrrolidone (povidone) and starch. Preferred binders include gelatin, sodium carboxymethyl cellulose and polyvinyl pyrrolidone (povidone). Polyvinyl pyrrolidone is quite especially preferred. Polyvinyl pyrrolidone (povidone) is commercially available in a suitable form, for example as Collidon 30.

The core can additionally contain carriers or fillers. Carbohydrates are suitable, for example. As examples, we may mention water-soluble carbohydrates, such as dextran, dextrin, dextrose (glucose), fructose, lactose, maltodextrin, mannitol, sucrose, sorbitol and xylitol. Another example of a carrier or filler is microcrystalline cellulose.

The core can contain other optional ingredients. It can additionally contain both water-soluble and water-insoluble excipients. These include preservatives, physical stabilizers and chemical stabilizers, such as acid, basic or buffering components. It can also contain wetting agents and solubilizers. The cores can additionally contain osmotically active substances. This is preferred in particular in the case of active substances that are only slightly water-soluble. In this case an osmotically active substance can serve as an entraining agent. The optional constituents also include antisticking agents.

In accordance with one preferred embodiment the core is constructed from a seed core not containing the active substance and a layer thereon that contains the active substance, the seed core preferably containing one or more carbohydrates and in particular being selected from sugar beads and beads of microcrystalline cellulose. The seed core may be water-soluble or contain water-soluble components. In accordance with another preferred embodiment the seed core is constructed from microcrystalline cellulose. Cores comprising seed core and layer containing the active substance preferably have an active substance layer that contains 50 wt. % or more, especially 60 wt. % or more, and more particularly 70 wt. % of active substance.

The pellet core can be coated with a protective layer. Preferred materials are water-soluble polymers, in particular hydroxypropyl methylcellulose.

According to the invention, the pellet cores, which are provided with the coating controlling the release of the active substance, should be as round as possible and as smooth as possible. So as to be able to verify the quality of pellet cores or pellets, an upper limit is therefore stipulated for the roughness. In order to determine the roughness of a pellet, the surface profile of a suitably selected segment is recorded, preferably using contactless optical methods, for example using an autofocusing laser profilometer, such as a UBM laser profilometer. Its mode of operation can be described as follows:

A laser beam is projected by a lens system onto the surface of the structure to be measured (the surface segment of a pellet core or pellet). The sensor head consists of a lens system and two photodetectors arranged symmetrically to its optical axis. At the level of the focal point of the lens system, a diaphragm is mounted, which trims the image of the laser beam on one side. If the sample is at the focus of the sensor, the laser beam reflected on the sample will be focused in the region of the diaphragm and will not be trimmed. In this case both detectors measure the same intensity. If the sample is outside of the focal range, no sharp image of the laser beam is produced. Instead, there is a wider intensity distribution in the region of the diaphragm, which is trimmed by the latter. Consequently, the detectors measure different intensities. To measure the height difference $\Delta h$ the sensor head is moved vertically until the sample is again in focus and both detectors measure the same intensity. The vertical displacement of the sensor, effected by means of magnetic positioning elements, then represents the height difference. While the sensor head measures the height of the sample continuously, the latter is moved along by a motorized x-y table under the sensor head. The lateral resolution of the profilometer is 0.5 µm, and is essentially determined by the beam diameter. The vertical accuracy is stated by the manufacturer to be 100 nm.

The surface segment to be measured is specified so as to cover typical profile structures. For example, for a spherical pellet with a radius between 400 and 600 µm, a surface region of 600 µm×600 µm can be scanned. Scanning takes place in thirteen parallel line scans at intervals of 50 µm. For the individual line scans, scanning is at intervals of 2.5 µm, which leads to a total number of 241 points per line scan.

Mathematical evaluation of the data is typically associated with data reduction. During the commencement of line scanning, the optical instrument must first achieve focusing on the surface. For this reason the first measurements suffer from uncertainties. Therefore the first fifteen measurement points of each line scan are excluded from the analysis. Because sometimes in the first line scans no convergence of the focusing procedure is achieved, possibly due to the fact that the starting point or end point of the line scan lies outside of the perimeter of the spherical particle, such line scans are excluded from the analysis. Similar focusing problems sometimes occur in the last line scans, which are then also excluded from the analysis.

The data from line scanning are thinned by a factor of 5, which leads to a reduction of the 241-15 measurement points per line to typically 45 measurement points per line. It has been found experimentally that this does not lead to any significant loss of a surface profile structure, since typical profile structures extend over 50 to 100 µm.

As already stated, a segment from an ideal spherical surface is then fitted, by the method of least squares, to the reduced set of data points. Deviations from the ideal surface are taken as a measure of the roughness. For this, a mean roughness $s_d$ can be defined.

This textural parameter corresponds to the usual definition of the root-mean-square roughness $R_{RMS}$, which is widely adopted for planar texturized surfaces. In addition, a relative root-mean-square roughness is also defined, which can be calculated from the mean roughness $s_d$ defined above and the radius of the sphere R according to $s_d/R$. The relative root-mean-square roughness is also stated as a percentage in the present application ($s_d/R \times 100\%$).

Pellet cores with a smooth surface, as described previously, are according to the invention provided with a coating, which controls the release of the active substance independently of the pH.

The coatings for pH-independent release of the active substance preferably contain a polymer, which is selected from ammonium-methacrylate copolymer, cellulose acetate-butyrate, cellulose acetate, cellulose acetate-propionate, ethyl cellulose, poly(ethylacrylate-methylacrylate) and polyvinyl acetate. Polyvinyl acetate is especially preferred. When using these film-forming agents, the release of the active substance from the pellets can be modified by the layer thickness of the applied film and by selection of suitable additional excipients (in particular pore-forming agents).

Accordingly, the coating for controlling the pH-independent release of the active substance can contain pore-forming agents, in particular water-soluble polymers or other water-soluble compounds.

The coating for controlling the pH-independent release of the active substance can also contain plasticizers. These include acetyltributyl citrate, triacetin, acetylated monoglyceride, rapeseed oil, olive oil, sesame oil, acetyltriethyl citrate, glycerol-sorbitol, diethyl oxalate, diethyl malate, diethyl fumarate, dibutyl succinate, diethyl malonate, dioctyl phthalate, dibutyl sebacate, diethyl citrate, tributyl citrate, glycerol, tributyrate, polyethylene glycol, propylene glycol and mixtures thereof.

The coating can also contain a separating agent. An example is talc.

In accordance with one preferred embodiment a pellet according to the invention comprises a core comprising the active substance and, applied to said core, a coating for controlling the release, the core being provided with the coating controlling the release in an amount from 30-70, preferably 40-60 wt. %, relative to the weight of the core. In accordance with a further embodiment the amount of the coating is 45-65 wt. %.

The pellets according to the invention can also have an outer protective coating. Preferred materials for this are water-soluble polymers, in particular hydroxypropyl methylcellulose.

Multiparticulate dosage forms can be provided using the pellets according to the invention. For example, capsules can be filled with the pellets. However, tablets can also be produced from the pellets.

Preferred Embodiments—Methods of Production

Methods of production are also provided according to the invention. These include methods for the production of pellet cores and methods for the coating of pellet cores, but the invention is not restricted to a particular manner of production.

One method for the production of pellet cores is fluidized-bed agglomeration. Granulation can be carried out without seed cores. In this way, pellet cores can be produced with a comparatively very high proportion of active substance. For example, pellet cores can be produced that contain 80 parts by weight or more, preferably 90 parts by weight or more, of active substance and in addition contain a binder. Using a sifting device, by means of which pellet cores are removed from the process continuously, it is possible to achieve a very narrow granulometric distribution. For example, a pellet core product can be obtained in which 95 wt. % or more, preferably 99 wt. % or more, of the pellet cores have a size between 100 and 300 μm or even between 200 and 300 μm.

For carrying out the method, a liquid, preferably aqueous solution or dispersion with an active substance and optionally one or more excipients, such as a binder, is injected from below into an empty fluidized-bed unit at the start of the process. Seed cores for pelletization are formed by spray-granulation. Through deposition of further material, the cores finally reach a size such that they are discharged from the unit via a sifting device.

Suitable equipment for carrying out fluidized-bed agglomeration is described in EP 163 836 B1, EP 332 031 B1 and EP 332 929 B1.

Another method for the production of pellet cores comprises the preparation of seed cores and the subsequent application of a layer of active substance (layering). The active substance (the metoprolol salt, preferably metoprolol succinate), optionally together with other ingredients, is applied to cores. This can take place in a fluidized-bed unit, with feed of a powdered material and a liquid, which binds the pulverulent ingredients to the cores. The powder can be the active substance (the metoprolol salt, preferably metoprolol succinate) or a mixture of the active substance and one or more excipients. The liquid can be water or an organic solvent; the liquid can also be a solution or dispersion.

In addition, a method for the production of pellet cores containing an active substance is preferred in which seed cores are coated, for example in fluidized-bed apparatus, with a solution or dispersion containing the active substance (the metoprolol salt, preferably metoprolol succinate) and optionally one or more excipients.

The production of pellet cores described above, by applying a layer of active substance on seed cores, preferably takes place in fluidized-bed apparatus with a Wurster insert (according to the Wurster process).

Another method for the production of pellet cores comprises the preparation of a powdered starting material in a first stage. The powdered starting material includes a carrier. The powdered starting material preferably undergoes treatment, for example in a shearing mixer, to break up aggregates. The powdered starting material can also be a mixture of a carrier and one or more other ingredients of the pellet cores that are being produced, for example binders. In this case the preparation of the powdered starting material typically involves mixing of the components.

It is preferable to use a powdered starting material with a limited grain size. In particular, the powdered starting material includes a carrier that has a limited grain size. Furthermore, a narrow granulometric distribution is preferred for the powdered starting material and in particular for the carrier.

For example, in the production of pellet cores with a size from 300 to 500 μm it has proved advantageous to use a powdered starting material, in particular a carrier, for which the oversize at a mesh size of 160 μm is less than 10 wt. % and in particular less than 5 wt. %. Powdered starting material, in particular a powdered carrier, are further preferred for which the oversize at a mesh size of 40 μm is in the range from 50 to 80 wt. %. Especially preferably, the oversize at a mesh size of 160 μm is in the range from 1 to 5 wt. % and at a mesh size of 40 μm is in the range from 50 to 70 wt. %.

The powdered starting material can be moistened before the pelletization stage. For this, a pharmaceutically acceptable diluent is added to it. It can be the same diluent as that used in the subsequent pelletization stage, or it can be a diluent of a different composition. The diluent can be an organic liquid. Preferably it is water or an aqueous solution or dispersion. The liquid can contain, as ingredients, a binder and/or the active substance (the metoprolol salt, preferably metoprolol succinate) and/or other core ingredients. The amount of the pharmaceutically acceptable diluent is preferably such that a wetted powdered starting material is achieved, with the amount of liquid added being less than the amount that is required for the formation of granulated structures. It is preferable to ensure uniform moistening of the powdered starting material. This can be carried out using a suitable mixer, such as a shearing mixer.

If several powdered components are used, mixing and pre-moistening can take place in one step, for example in a high-speed mixer.

In the pelletization stage, pellets are formed from the optionally premoistened starting material, with addition of a pharmaceutically acceptable liquid diluent. The diluent must meet the same quality criteria as for the diluent used for premoistening.

The diluent can contain the active substance (the metoprolol salt, preferably metoprolol succinate).

It is also possible to add powdered ingredients, for example powdered active substance, during pelletization, if the process ensures homogeneous, thorough mixing. As the pellets according to the invention contain the active substance (the metoprolol salt, preferably metoprolol succinate), this must either be present in the powdered starting material or it must be added during pelletization as a constituent of the diluent or in powdered form. Combinations of these measures are also possible.

According to a preferred embodiment, the method comprises the following stages:
(a) preparation of a powdered starting material, which includes a carrier;
(b) feed of the powdered starting material, which is optionally wetted with a pharmaceutically suitable liquid diluent, into a device that has:
a rotary chamber with a cylindrical wall extending axially,
a device for leading air through the rotary chamber from the bottom,
a spraying device for feeding liquid into the chamber,
one or more inlets for introducing the powdered mixture,
a rotor, which rotates about a vertical axis, the rotor being arranged in the rotary chamber, and has a central horizontal surface and, in at least the outer third of the rotor, the form of a conical surface with a slope, directed outward and upward, between 10° and 80°, with the conical surface having a circular upper edge, which is in a plane that is perpendicular to the axis of rotation,
a multiplicity of guide vanes each with an outer end that is fixed statically to the cylindrical wall of the rotary chamber above the plane that is formed by the upper edge of the conical surface of the rotor, and an inner end, which extends into the rotary chamber and is arranged tangentially to the cylindrical wall of the rotary chamber and has, in cross-section to the axis of rotation, essentially the form of a circular arc or a spiral,
(c) rotation of the rotor, so that the product, which is circulated for a sufficient length of time through kinetic energy, moves from the rotor to the inner surface of the guide vanes, before it drops back onto the rotor, while optionally air is supplied and/or a pharmaceutically acceptable liquid is sprayed into the rotary chamber, so that solid pellets with a desired diameter are formed.

A suitable device for carrying out the first method for the production of pellet cores is described in DE 197 50 042 A1.

During pellet formation, a pharmaceutically acceptable diluent is supplied, as already described. The amount is selected depending in particular on the components of the starting material, the desired pellet size and other operational variables, for example the amount of air supplied.

The pellet cores finally obtained are dried.

It is preferable to verify whether the pellet cores produced satisfy the requirements of the invention. In particular it is verified whether a pellet core product according to the invention is produced. This means that preferably the pellets of the pellet core product obtained, which consists of a collection or a multiplicity of pellet cores, are primarily spherical and have smooth surfaces. Preferably at least 90% of the pellet cores of a pellet core product fulfill the requirements according to the invention regarding spherical shape and smooth surface.

The pellets obtained can find application as a pellet product that comprises a multiplicity of pellets. A pellet product comprises a collection of pellets, typically 50 or more, preferably 100 or more pellets. A pellet product according to the invention comprises primarily pellets that fulfill the criteria according to the invention. Preferably at least 90%, in particular at least 95% and quite especially preferably at least 98% of the pellets have a length-width ratio of less than about 1.4, preferably less than about 1.3, more preferably less than about 1.2, even more preferably less than about 1.1 and in particular less than about 1.05. Pellets that have the preferred length-width proportions, preferably also meet the other requirements for pellets according to the invention, and especially the requirements that are specified in the claims and in the description.

The pellet cores obtained according to one of the above methods can optionally be provided with one or more coatings by known methods. These include coatings obtained from water-soluble film-forming agents.

The pellet cores—with or without coating, such as a coating obtained from a water-soluble film-forming agent, are coated with a polymer for pH-independent release of the active substance.

According to the invention, tablets can also be produced, by compressing pharmaceutical pellets, optionally together with excipients. It is then possible, according to the invention, to obtain tablets for which the release curve of the active substance has undergone approximately parallel displacement in comparison with the release curve from the pellets. In other words the lag-phase that arises during release from the tablets is shorter than the lag-phase arising during release from the pellets, whereas the gradient of the release curve remains essentially unchanged. The release behavior can be measured, as has already been described.

Tablets can be produced, for example, with a compression force between 2 and 30 kN. Tablet hardnesses between 20 N and over 200 N can be achieved.

The invention is explained by the following production examples, examples and test examples. Metoprolol succinate is used as the active substance.

Production Example 1

The example relates to the production of pellets containing metoprolol succinate.

The following starting materials are used for the production of pellet cores with the active substance metoprolol succinate:

| | |
|---|---|
| Seed cores: Sugar Spheres NF (Pharm-(a)-spheres, 212-300 μm) | 300 g |
| Colloidal silica (Syloid 244 FP) | 45 g |
| Metoprolol succinate | 1200 g |
| Demineralized water | 2757 g |

A proportion of the demineralized water (2457 g) is heated to approx. 60° C. The metoprolol succinate is dissolved in the heated water. The silica (Syloid 244 FP) is suspended in another portion of the demineralized water (300 g) using a homogenizer for ten minutes. Then the silica dispersion is poured into the solution of active substance. The resultant mixture (coating dispersion) is stirred at a temperature of approx. 50° C.

For coating, the seed cores are put in a fluidized-bed coating device (Glatt GPCG 1). Then the coating dispersion is sprayed on at an initial spraying rate of 6 g/min. The spraying rate is then increased to 8-10 g/min. The inlet air temperature during coating is approx. 55° C.

After the coating dispersion has been sprayed on, the cores obtained are dried in the apparatus for ten minutes at an inlet air temperature of approx. 60° C. Then the cores are taken out and dried further at 45° C. overnight.

In the manner described above, metoprolol succinate cores can be obtained with a content of active substance of 77.67 wt. %.

The cores obtained, containing the active substance, can be provided with a coating that controls the pH-independent release of the active substance. Polyvinyl acetate is a suitable coating material. Example preparation starts from the following starting materials:

| | |
|---|---|
| Metoprolol succinate cores (as described above) | 300.00 g |
| Polyvinyl acetate dispersion (solids content: 416.7 g) (Kollicoat SR 30 D) | 125.0 g |
| Triethyl citrate | 12.5 g |
| Talc | 12.5 g |
| Demineralized water | 420.00 g |

To prepare the coating dispersion, triethyl citrate and talc are dispersed in the demineralized water for ten minutes using a homogenizer. The polyvinyl acetate dispersion is passed through a suitable sieve to separate out possible agglomerates and the dispersion of excipients obtained previously is added to it, stirring slowly. The coating dispersion obtained is stirred for one hour, before the film coating of the cores is begun.

The coating is applied in a fluidized-bed coating device (Glatt GPCG 1). The cores containing the active substance are heated to approx. 30° C. Then the coating dispersion is sprayed on at a spraying rate of approx. 7-8 g/min. The inlet air temperature is approx. 35° C.

In the same conditions as previously, a protective coating is applied, using the following excipients in the following amounts:

| | |
|---|---|
| Hydroxypropyl methylcellulose (Methocel E5) | 0.55 g |
| Colloidal silica (Syloid 244FP) | 3.49 g |
| Demineralized water | 70.00 g |

Hydroxypropyl methylcellulose is dissolved in the water, and then the silica is added in portions, with stirring. After applying this dispersion on the coated pellets, the pellets are taken out of the fluidized-bed apparatus. The pellets can then be finish-dried in a ventilated stove.

Production Example 2

The example relates to the production of pellets containing metoprolol succinate and the further processing of the pellets to tablets. The pellets are provided with 50 wt. % of a coating that controls the release. The tablets are produced in four different dose strengths (23.75; 47.5; 95 and 190 mg of metoprolol succinate). The formulations are shown in the table below.

| | | Dose strength (mg) | | | |
|---|---|---|---|---|---|
| Stage | Component | 23.75 | 47.5 | 95 | 190 |
| Application of active substance to seed cores (layering) | Metoprolol succinate | 23.8 | 47.5 | 95.0 | 190.0 |
| | Colloidal silica (Syloid 244 FP) | 0.9 | 1.8 | 3.6 | 7.1 |
| | Sugar Spheres NF (Pharm-(a)-spheres, 212-300 μm) | 5.9 | 11.9 | 23.8 | 47.5 |
| Coating for controlled release | Polyvinyl acetate dispersion (Kollicoat SR 30 D), solids content | 12.7 | 25.5 | 51.0 | 101.9 |
| | Talc | 1.3 | 2.5 | 5.1 | 10.2 |
| | Triethyl citrate | 1.3 | 2.5 | 5.1 | 10.2 |
| Protective coating | Hydroxypropylmethyl-cellulose (Methocel E5) | 0.1 | 0.1 | 0.2 | 0.5 |
| | Colloidal silica (Syloid 244 FP) | 0.4 | 0.8 | 1.6 | 3.2 |
| Mixing | Microcrystalline cellulose (Avicel PH 200) | 4.2 | 8.5 | 16.9 | 33.8 |
| | Microcrystalline cellulose (Avicel PH 101) | 31.0 | 62.0 | 124.1 | 248.1 |
| | Croscarmellose-sodium (Nymzel ZSX) | 2.5 | 5.1 | 10.1 | 20.2 |
| Final mixing | Magnesium stearate | 0.2 | 0.3 | 0.7 | 1.3 |
| Film coating | Water-soluble coating (HPMC 2910, 3 cP, 30%; HPMC 2910, 6 cP, 30%; titanium dioxide, 20%, talc, 10%, Macrogol 400, 5%; Macrogol 6000, 5%) (Opadry 05B28447) | 4.5 | 9.0 | 13.5 | 18.0 |
| Total weight of the film-coated tablet | | 88.8 | 177.5 | 350.5 | 692.0 |

The production of pellet cores with the active substance metoprolol succinate takes place in the same way as in production example 1.

The pellet cores containing active substance are provided with a coating for controlled release. Subsequently a protective coating is applied to the pellets. The pellets obtained are then used for producing tablets. The tableting phase contains the excipients indicated in the table above. The pellets provided with the active substance release-controlling coating and with the protective coating are mixed with the stated excipients in two steps and are pressed to tablets.

The tablets, finally, are additionally provided with a water-soluble coating.

Production Example 3

In a manner analogous to that of preparation example 2, tablets are produced on the basis of pellets which have been provided with 60 wt. % of a release-controlling coating. Details of the formulations are given in the following table.

| Stage | Component | Dosage strength (mg) | | | |
|---|---|---|---|---|---|
| | | 23.75 | 47.5 | 95 | 190 |
| Application of active substance to seed cores (layering) | Metoprolol succinate | 23.8 | 47.5 | 95.0 | 190.0 |
| | Colloidal silica (Syloid 244 FP) | 0.9 | 1.8 | 3.6 | 7.1 |
| | Sugar Spheres NF (Pharm-(a)-spheres, 212-300 μm) | 5.9 | 11.9 | 23.8 | 47.5 |
| Coating for controlled release | Polyvinyl acetate dispersion (Kollicoat SR 30 D), solids content | 15.3 | 30.6 | 61.2 | 122.3 |
| | Talc | 1.5 | 3.1 | 6.1 | 12.2 |
| | Triethyl citrate | 1.5 | 3.1 | 6.1 | 12.2 |
| Protective coating | Hydroxypropylmethyl-cellulose (Methocel E5) | 0.1 | 0.1 | 0.3 | 0.6 |
| | Colloidal silica (Syloid 244 FP) | 0.4 | 0.8 | 1.6 | 3.2 |
| Mixing | Microcrystalline cellulose (Avicel PH 200) | 1.2 | 2.3 | 4.6 | 9.2 |
| | Microcrystalline cellulose (Avicel PH 101) | 31.0 | 62.0 | 124.1 | 248.1 |
| | Croscarmellose-sodium (Nymzel ZSX) | 2.5 | 5.1 | 10.1 | 20.2 |
| Final mixing | Magnesium stearate | 0.2 | 0.3 | 0.7 | 1.3 |
| Film coating | Water-soluble coating (HPMC 2910, 3 cP, 30%; HPMC 2910, 6 cP, 30%; titanium dioxide, 20%, talc, 10%, Macrogol 400, 5%; Macrogol 6000, 5%) (Opadry 05B28447) | 4.5 | 9.0 | 13.5 | 18.0 |
| Total weight of the film-coated tablet | | 88.8 | 177.5 | 350.5 | 692.0 |

Production Example 4

Pellets are produced with 45 wt. %, 50 wt. % and 60 wt. % of a coating for controlled release. Production takes place in the same way as for the production examples above. The formulations are indicated in the table below.

| Component | 45% coating (batch: 0425/2006) Mass (mg) | 50% coating (batch: 0357/2006) Mass (mg) | 60% coating (batch: 0348/2006) Mass (mg) |
|---|---|---|---|
| Metoprolol succinate | 190.00 | 190.00 | 190 |
| Colloidal silica (Syloid 244 FP) | 7.13 | 7.13 | 7.13 |
| Sugar Spheres NF (Pharm-(a)-spheres, 212-300 μm) | 47.50 | 47.50 | 47.50 |
| Pellets with active substance layer, total | 244.63 | 244.63 | 244.63 |
| Coating for controlled release | | | |
| Pellets with active substance layer | 244.63 | 244.63 | 244.63 |
| Polyvinyl acetate dispersion (Kollicoat SR 30 D), solids content | 91.74 | 101.93 | 122.32 |
| Talc | 9.17 | 10.19 | 12.23 |
| Triethyl citrate | 9.17 | 10.19 | 12.23 |
| Pellets with coating for controlled release, total | 354.71 | 366.94 | 391.41 |
| Protective coating (1%) | | | |
| Pellets with coating for controlled release | 354.71 | 366.94 | 391.41 |
| Hydroxypropylmethyl-cellulose (Methocel E5) | 0.46 | 0.48 | 0.51 |

-continued

| Component | 45% coating (batch: 0425/2006) Mass (mg) | 50% coating (batch: 0357/2006) Mass (mg) | 60% coating (batch: 0348/2006) Mass (mg) |
| --- | --- | --- | --- |
| Colloidal silica (Syloid 244 FP) | 3.09 | 3.20 | 3.41 |
| Pellets with protective coating, total | 358.26 | 370.62 | 395.33 |

Production Example 5

Using coated pellets as obtained in production example 4, tablets are produced. Production takes place in the same way as for the production examples above. The formulations are indicated in the tables below.

| Tablets based on pellets with 45% coating for controlled release | Batch size (kg) | Amount (%) | Strength: 23.75 mg Dose unit (mg) | Strength: 47.5 mg Dose unit (mg) | Strength: 95 mg Dose unit (mg) | Strength: 190 mg Dose unit (mg) |
| --- | --- | --- | --- | --- | --- | --- |
| Coated pellets (45%) | 2.392 | 53.15 | 44.78 | 89.56 | 179.13 | 358.25 |
| Microcrystalline cellulose (Avicel PH 200) | 0.308 | 6.85 | 5.77 | 11.54 | 23.07 | 46.15 |
| Microcrystalline cellulose (Avicel PH 101) | 1.656 | 36.80 | 31.00 | 62.01 | 124.02 | 248.03 |
| Croscarmellose-sodium (Nymcel ZSX) | 0.135 | 3.00 | 2.53 | 5.06 | 10.11 | 20.22 |
| Magnesium stearate | 0.009 | 0.20 | 0.17 | 0.34 | 0.67 | 1.35 |
| Total | 4.500 | 100.00 | 84.25 | 168.50 | 337.00 | 674.00 |

| Tablets based on pellets with 50% coating for controlled release | Batch size (kg) | Amount (%) | Strength: 23.75 mg Dose unit (mg) | Strength: 47.5 mg Dose unit (mg) | Strength: 95 mg Dose unit (mg) | Strength: 190 mg Dose unit (mg) |
| --- | --- | --- | --- | --- | --- | --- |
| Coated pellets (50%) | 2.475 | 55.00 | 46.34 | 92.68 | 185.35 | 370.70 |
| Microcrystalline cellulose (Avicel PH 200) | 0.225 | 5.00 | 4.21 | 8.43 | 16.85 | 33.70 |
| Microcrystalline cellulose (Avicel PH 101) | 1.656 | 36.80 | 31.00 | 62.01 | 124.02 | 248.03 |
| Croscarmellose-sodium (Nymcel ZSX) | 0.135 | 3.00 | 2.53 | 5.06 | 10.11 | 20.22 |
| Magnesium stearate | 0.009 | 0.20 | 0.17 | 0.34 | 0.67 | 1.35 |
| Total | 4.500 | 100.00 | 84.25 | 168.50 | 337.00 | 674.00 |

| Tablets based on pellets with 60% coating for controlled release | Batch size (kg) | Amount (%) | Strength: 23.75 mg Dose unit (mg) | Strength: 47.5 mg Dose unit (mg) | Strength: 95 mg Dose unit (mg) | Strength: 190 mg Dose unit (mg) |
| --- | --- | --- | --- | --- | --- | --- |
| Coated pellets (60%) | 2.639 | 58.65 | 49.42 | 98.83 | 197.67 | 395.33 |
| Microcrystalline cellulose (Avicel PH 200) | 0.061 | 1.35 | 1.14 | 2.28 | 4.55 | 9.10 |
| Microcrystalline cellulose (Avicel PH 101) | 1.656 | 36.80 | 31.00 | 62.00 | 124.00 | 248.00 |
| Croscarmellose-sodium (Nymcel ZSX) | 0.135 | 3.00 | 2.53 | 5.05 | 10.10 | 20.20 |
| Magnesium stearate | 0.009 | 0.20 | 0.18 | 0.35 | 0.70 | 1.40 |
| Total | 4.500 | 100.00 | 84.25 | 168.50 | 337.00 | 674.00 |

All of the tablets can additionally be coated with the film set out in production example 3.

Example 1

The example relates to investigation of the release behavior of products according to the invention. In particular it is shown that the release profile can be adjusted by providing pellet cores according to the invention with coatings that control the release, and varying the amount of the coatings.

Release was determined in each case with a paddle apparatus (USP/Ph.Eur.) at a stirring speed of 50 revolutions per minute in phosphate buffer pH 6.8 as test medium at a temperature of 37° C.

First pellets were produced with the active substance metoprolol succinate, as was described above. The thickness of the coating was varied by using different amounts of coating dispersion with polyvinyl acetate and 10 wt. % talc and 10 wt.

% triethyl citrate, based in each case on the amount of solid polyvinyl acetate. Relative to the pellet cores containing the active substance, these amounts in the individual experiments were 50 or 60 wt. %. The pellets were in addition provided with a coating of hydroxypropyl methylcellulose and colloidal silica.

Figure 1:
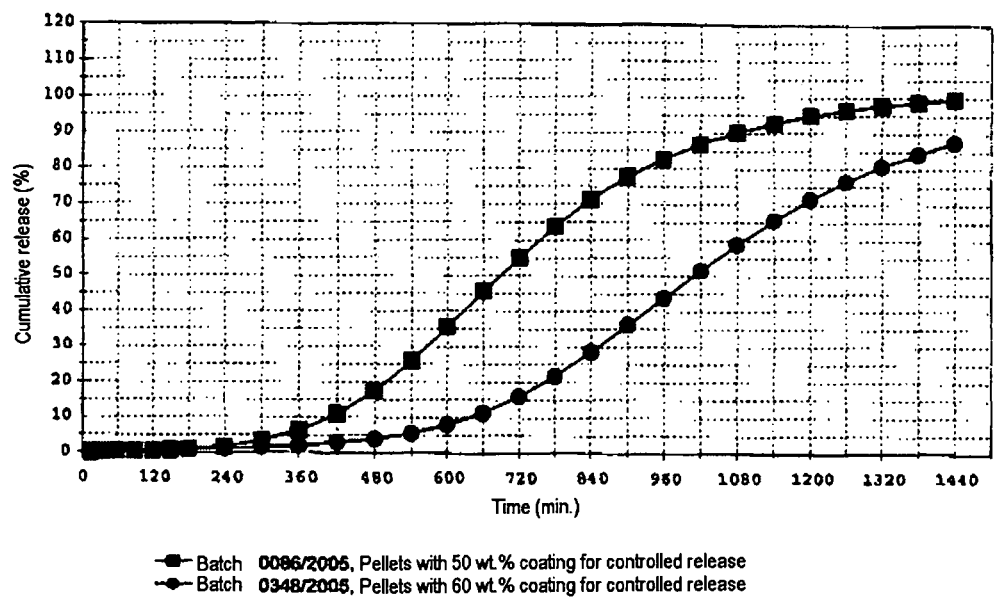
FIG. 1 shows the influence of the thickness of the release-controlling coating on the release of the active substance in the case of pellets containing the active substance metoprolol succinate, with the coating consisting of polyvinyl acetate and, relative to the weight of the polyvinyl acetate, 10 wt. % triethyl citrate and 10 wt. % talc. The cumulative release (%)

Samples of the individual preparations were then submitted to release tests. The results are shown in FIG. 1.

Example 2

The example relates to investigation of the release behavior of products according to the invention. In particular the example elucidates the effect of tableting on the release behavior.

First, pellets were produced with the active substance metoprolol succinate, as was described above. The release behavior of these pellets is shown in FIG. 1.

In addition, tablets were produced from the pellets, as was explained in production examples 2 and 3. The release behavior of the tablets was investigated, as described in example 1, and is shown in FIG. 2.

Example 3

The release behavior of tablets with a dose strength of 23.75 mg, whose production was elucidated in production example 2, was investigated. The method employed was that described in example 1. The results are shown in FIG. 3.

Example 4

The release behavior of pellets with a dose strength of 190 mg, whose production was elucidated in production example 4, was investigated. The method employed was that described in example 1. The results are shown in FIG. 16.

Example 5

The release behavior of tablets with a dose strength of 190 mg, whose production was elucidated in production example 5, was investigated. The method employed was that described in example 1. The results are shown in FIG. 17. The tablets of batch 0463/2006 are tablets with a strength of 190 mg based on pellets with a 45 wt. % coating for controlled release. The tablets of batch 0377/2006 are tablets with a strength of 190 mg based on pellets with a 50 wt. % coating for controlled release. The tablets of batch 0498/2006 are tablets with a strength of 190 mg based on pellets with a 60 wt. % coating for controlled release.

Test Examples

The following examples relate to investigation of pellet cores for determining the surface roughness. They serve to illustrate the methods used in this case Test Example 1

Figure 6A:
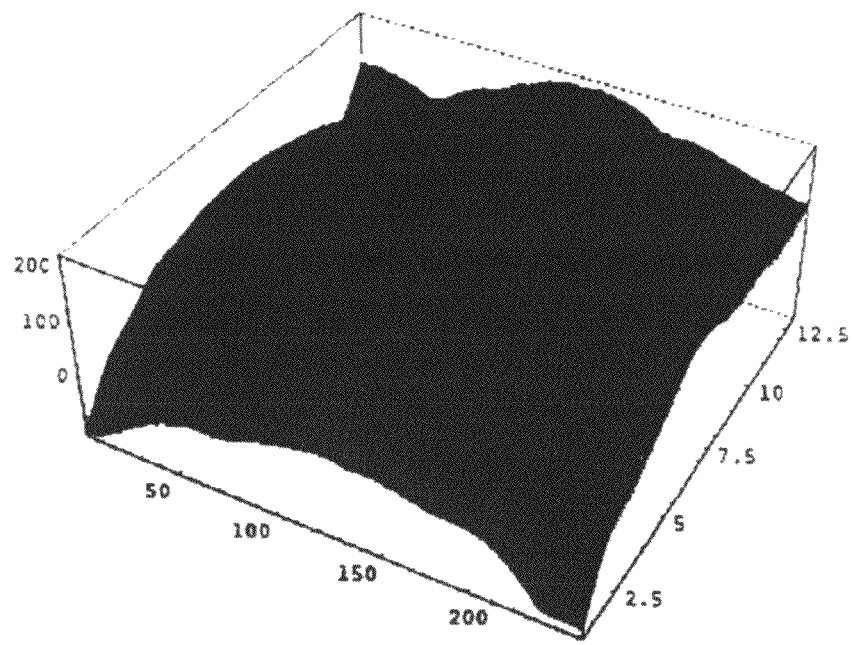
Figure 6B:
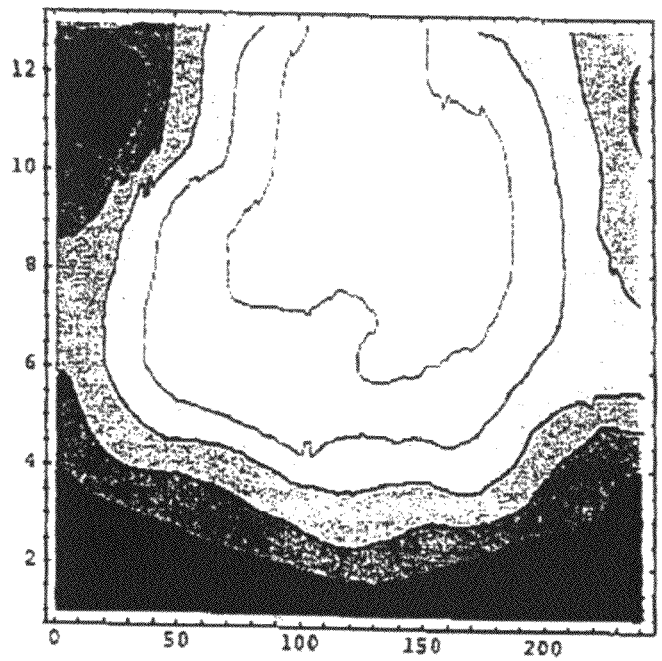
Figure 6C:
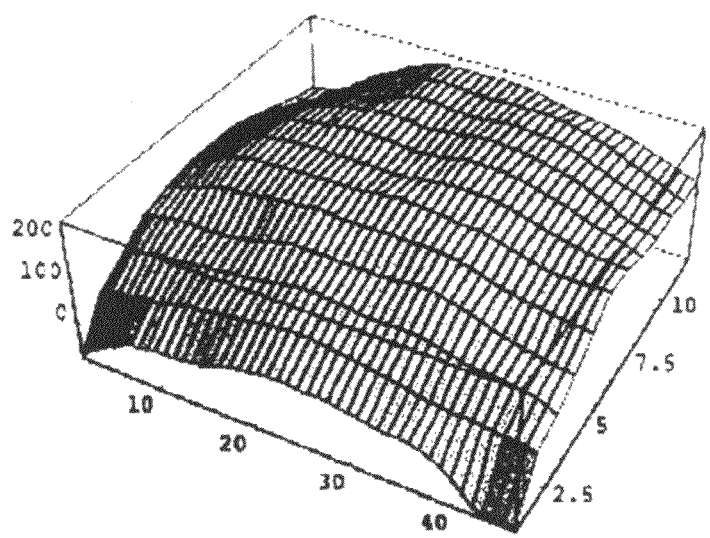
Figure 6D:
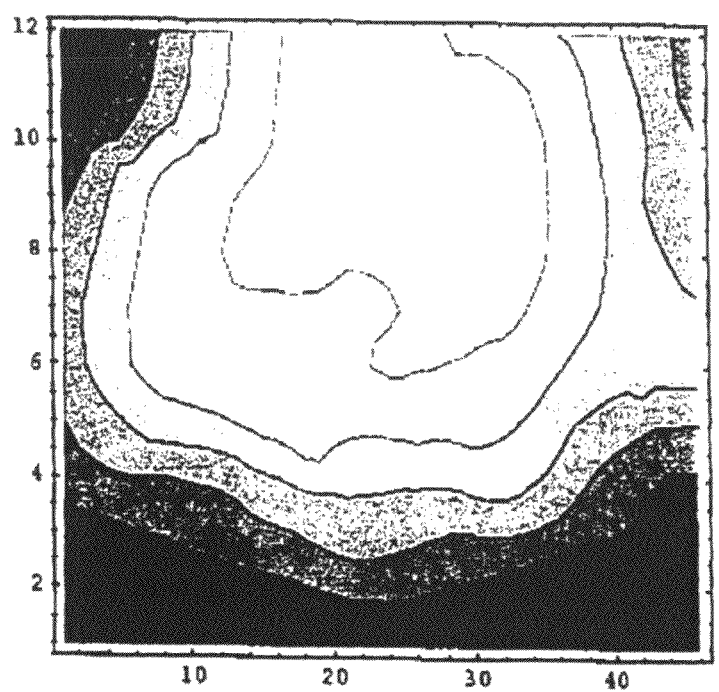

Pellets with the batch designation SFD E 0724 were investigated. An electron micrograph of pellets of this kind is shown in FIG. 5. A segment from the surface of a pellet from this batch was scanned with a laser profilometer, as described previously. A graphical representation of the measurement results is shown in FIG. 6A as a surface graph and in FIG. 6B as a contour diagram. The roughness was calculated using a reduced data set, as described previously. A surface graph based on the reduced data set is shown in FIG. 6C, and the corresponding contour diagram is shown in FIG. 6D.

Figure 6E:
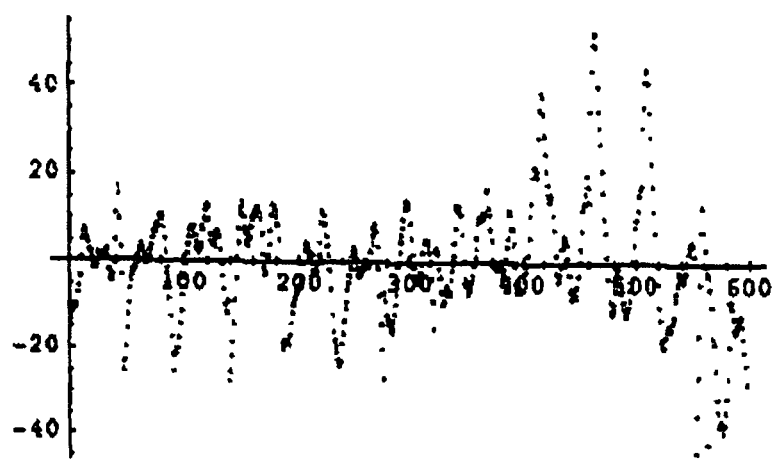

Using the method of least squares, a sphere was determined that provides an optimum representation of the measurement points of the reduced set. The coordinates of the center of this sphere were determined as 385 µm; 324 µm and −293 µm. The optimum radius R was 516 µm. The distribution of the data after adjustment is shown in FIG. 6E. In this diagram the horizontal axis denotes the measured data points. The vertical axis denotes the distance of the measured points of the profile from the surface of the ideal sphere with the coordinates of the center and the radius as stated previously. The data points are distributed uniformly above and below the horizontal axis.

Statistical analysis of the data shows that the mean roughness ad has a value of 13.6 µm and that the relative mean roughness $\sigma_d/R$ has a value of 2.64%. The absolute roughness has a value of more than 50 µm. The pellet core investigated therefore does not fulfill the criteria according to the invention for a pellet core with a smooth surface.

Test Example 2

Figure 7A:
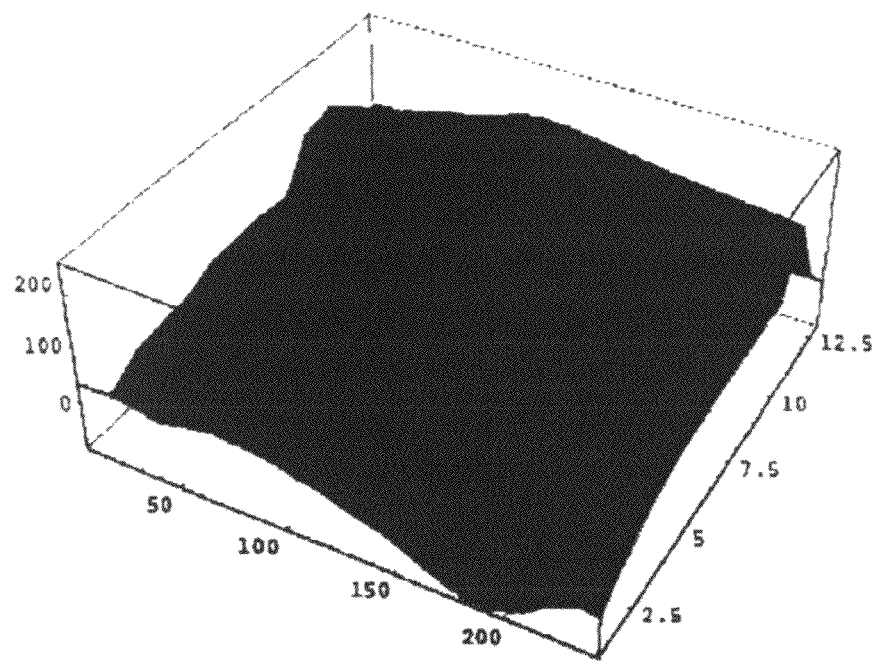
Figure 7B:
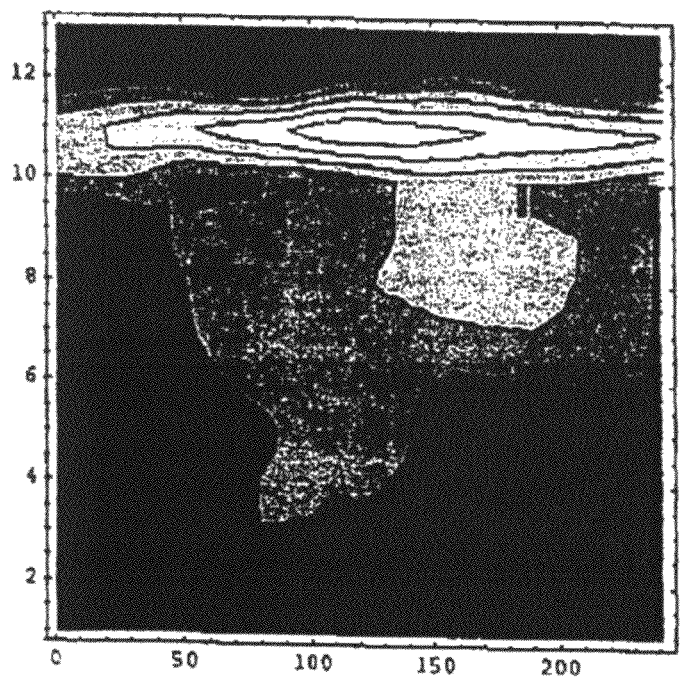
Figure 7C:
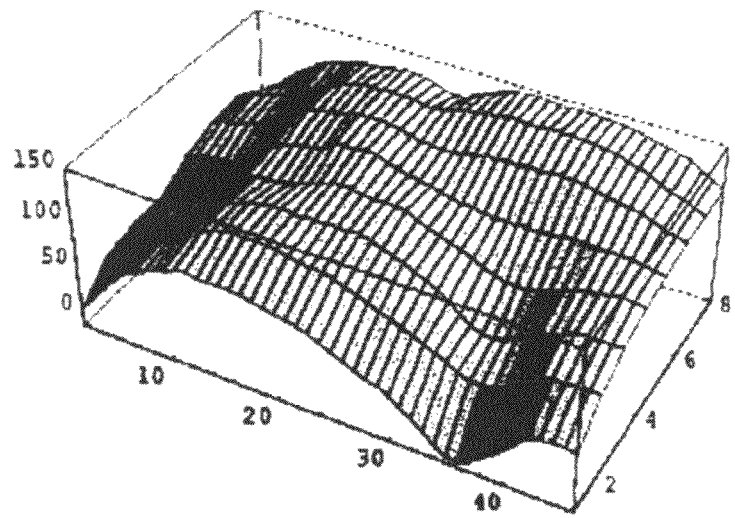
Figure 7D:
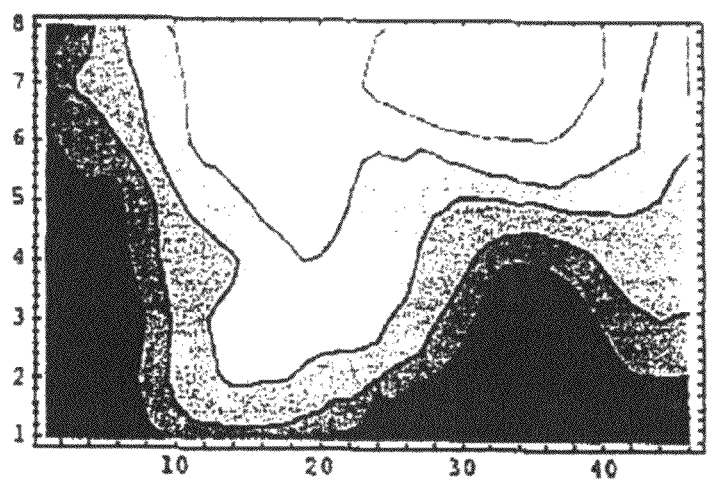

Another pellet from the same batch already mentioned in test example 1 was investigated in the same way as described previously. A graphical representation of the measurement results is shown in FIG. 7A as a surface graph and in FIG. 7B as a contour diagram. The reduced data set that was used for calculating the roughness forms the basis of the surface graph shown in FIG. 7C, and of the contour diagram shown in FIG. 7D.

Figure 7E:
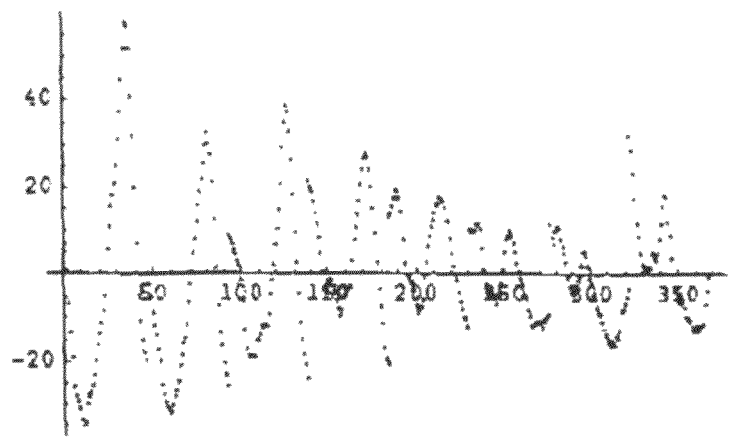

Using the method of least squares, a sphere was determined that provides an optimum representation of the measurement points of the reduced set. The coordinates of the center of this sphere were determined as 434 µm; 336 µm and −841 µm. The optimum radius R was 983 µm. The distribution of the data after adjustment is shown in FIG. 7E. Statistical analysis of the data shows that the mean roughness $\sigma_d$ has a value of 15.9 µm and the relative mean roughness $\sigma_d/R$ has a value of 1.62%. The absolute roughness has a value of more than 50 µm. The pellet core investigated therefore does not fulfill the criteria according to the invention for a pellet core with a smooth surface.

Test Example 3

Figure 9A:
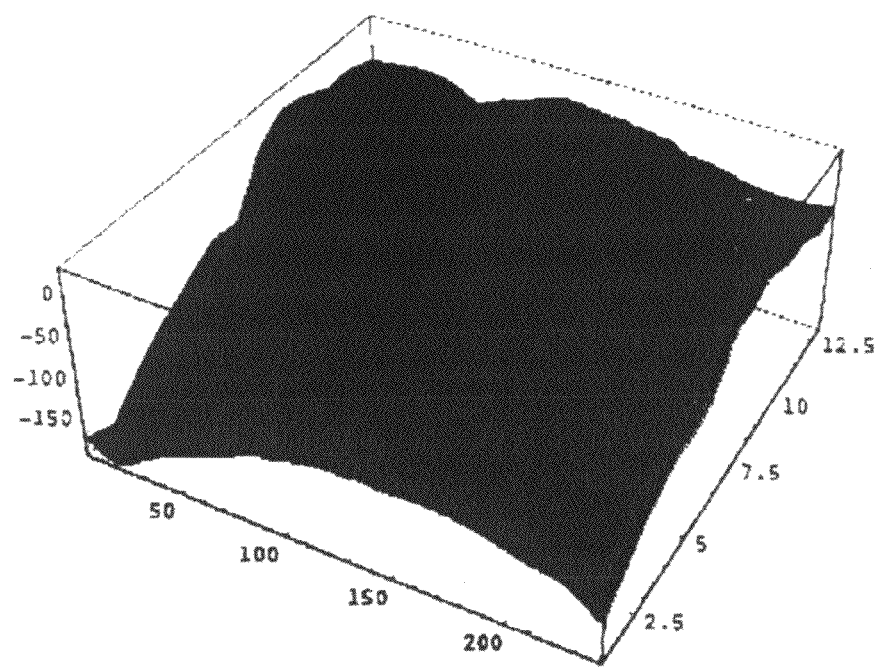
Figure 9B:
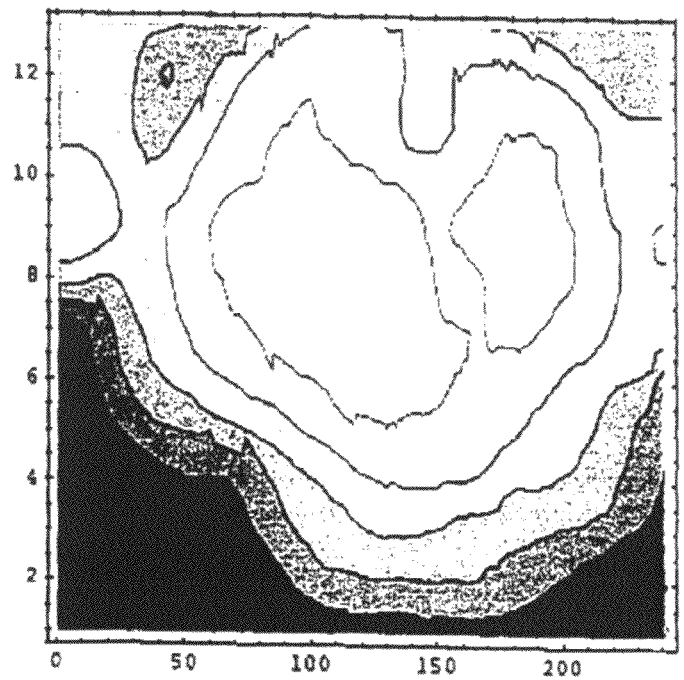
Figure 9C:
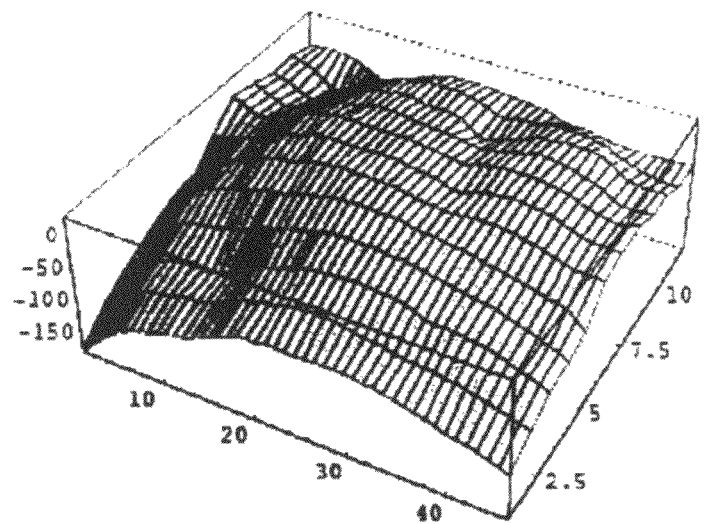
Figure 9D:
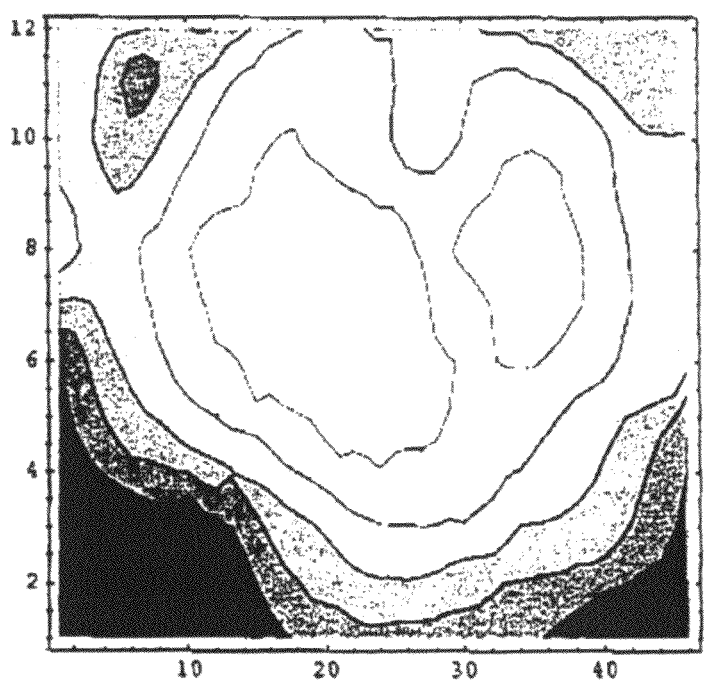

Pellets with the batch designation SFD E 0718 were investigated. An electron micrograph of pellets of this kind is shown in FIG. 8. A segment from the surface of a pellet from this batch was scanned with a laser profilometer, as described previously. A graphical representation of the measurement results is shown in FIG. 9A as a surface graph and in FIG. 9B as a contour diagram. The roughness was calculated using a reduced data set, as described previously. A surface graph based on the reduced data set is shown in FIG. 9C, and the corresponding contour diagram is shown in FIG. 9D.

Figure 9E:
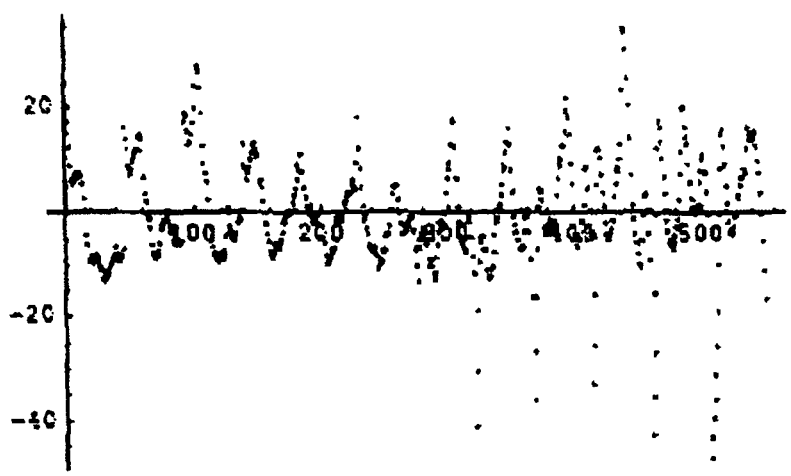

Using the method of least squares, a sphere was determined that provides an optimum representation of the measurement points of the reduced set. The coordinates of the center of this sphere were determined as 391 µm; 337 µm and −680 µm. The optimum radius R was 713 µm. The distribution of the data after adjustment is shown in FIG. 9E. Statistical analysis of the data shows that the mean roughness ad has a value of 10.7 µm and the relative mean roughness $\sigma_d/R$ has a value of 1.5%. The absolute roughness has a value of about 50 µm. The pellet core investigated therefore does not fulfill the criteria according to the invention for a pellet core with a smooth surface.

Test Example 4

Figure 10A:
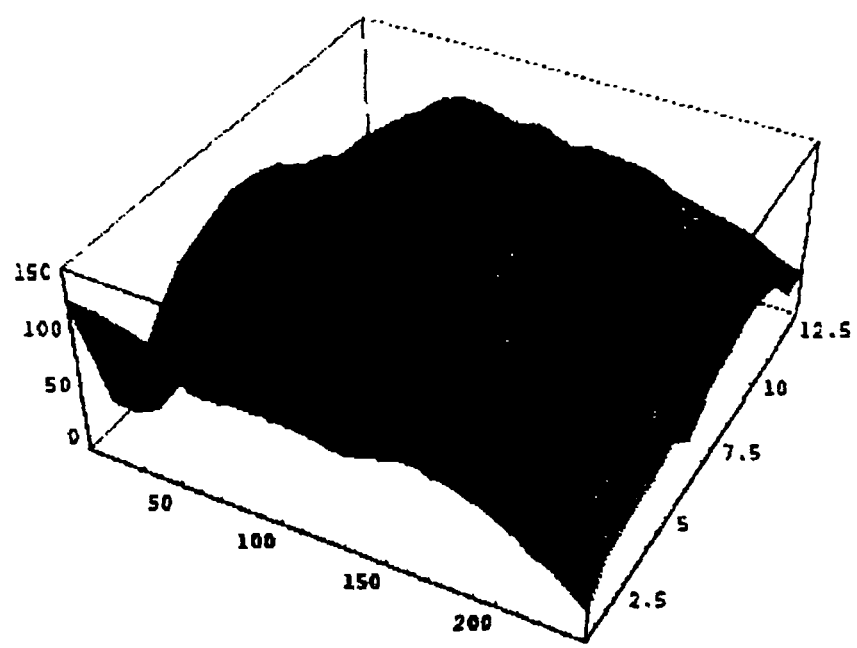
Figure 10B:
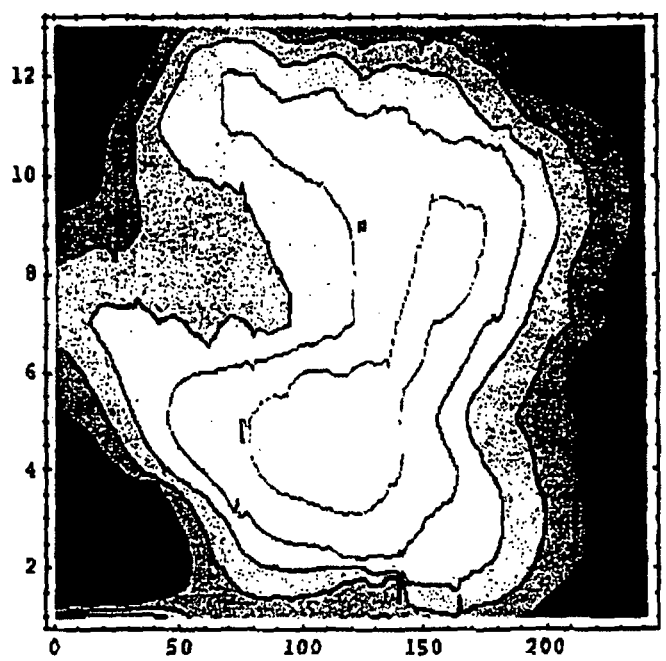
Figure 10C:
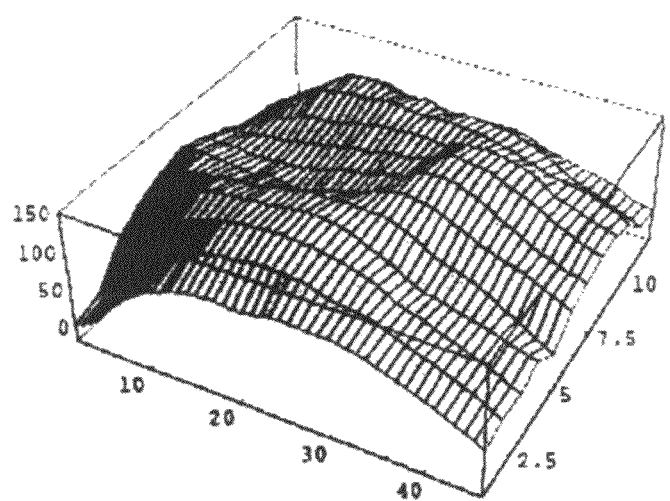
Figure 10D:
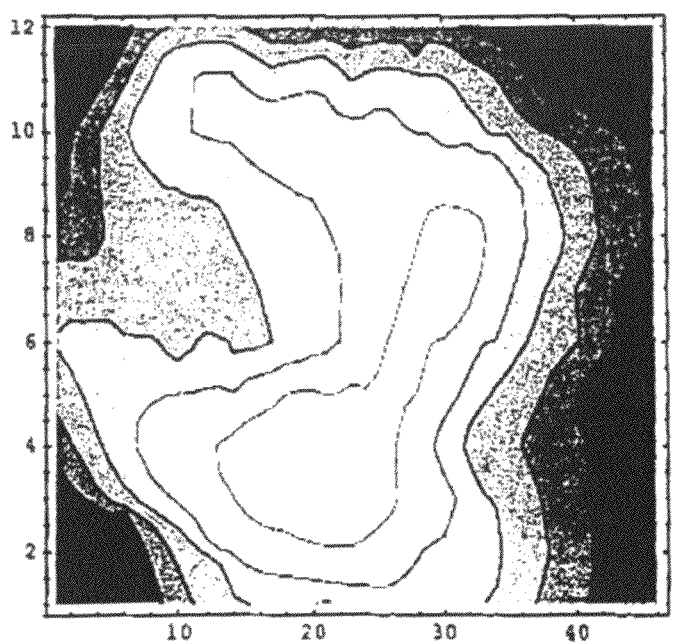

Another pellet from the same batch already mentioned in test example 3 was investigated in the same way as described previously. A graphical representation of the measurement results is shown in FIG. 10A as a surface graph and in FIG. 10B as a contour diagram. The reduced data set that was used for calculating the roughness forms the basis of the surface graph shown in FIG. 10C, and of the contour diagram shown in FIG. 10D.

Figure 10E:
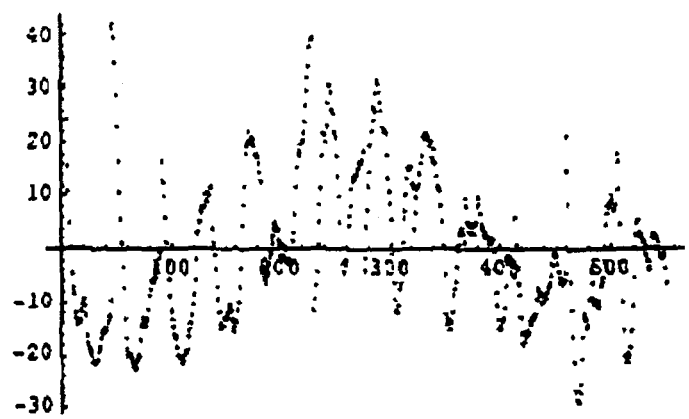

Using the method of least squares, a sphere was determined that provides an optimum representation of the measurement points of the reduced set. The coordinates of the center of this sphere were determined as 309 µm; 297 µm and −656 µm. The optimum radius R was 804 µm. The distribution of the data after adjustment is shown in FIG. 10E. Statistical analysis of the data shows that the mean roughness ad has a value of 14.31 µm and the relative mean roughness $\sigma_d/R$ has a value of 1.78%. The absolute roughness has a value of 45 µm. The pellet core investigated therefore does not fulfill the criteria according to the invention for a pellet core with a smooth surface.

Test Example 5

Figure 12A:
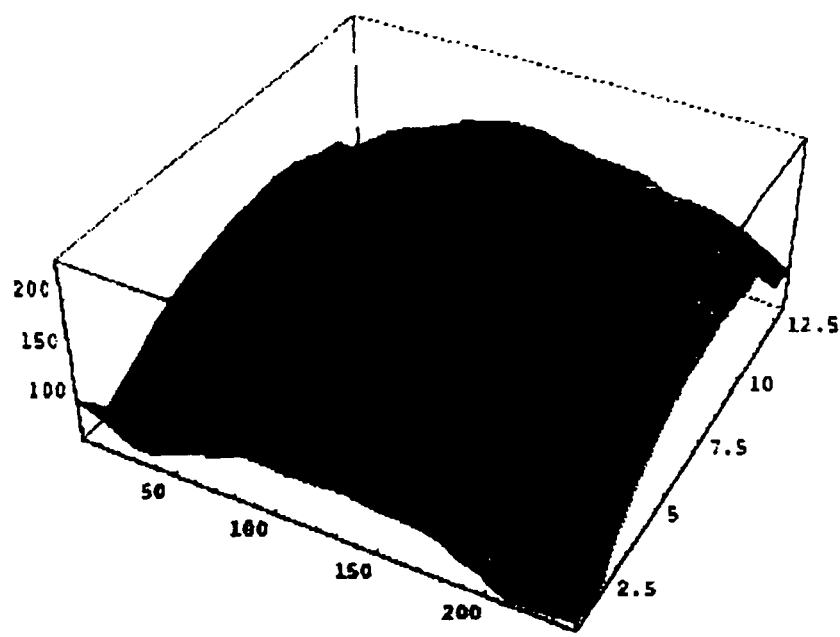
Figure 12B:
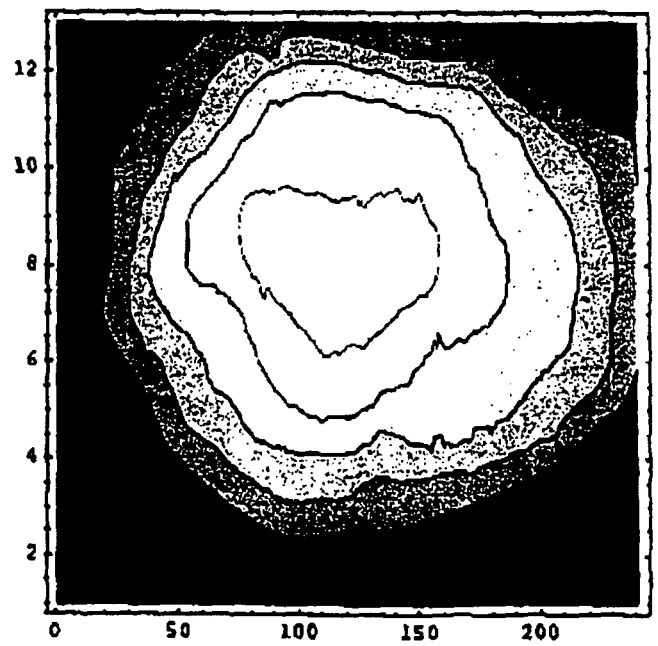
Figure 12C:
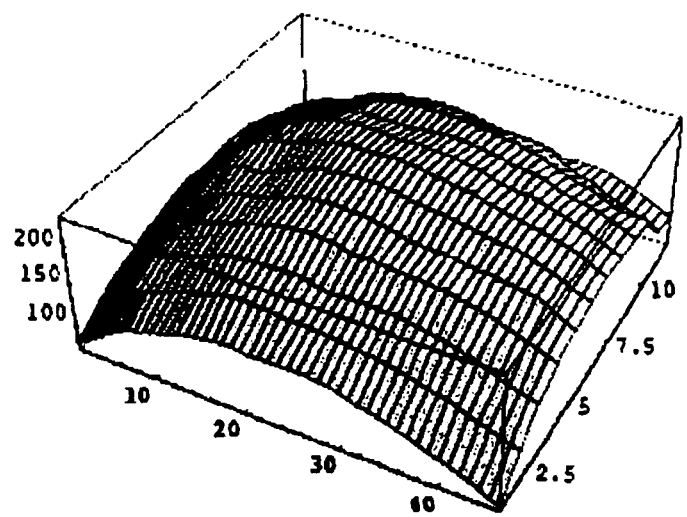
Figure 12D:
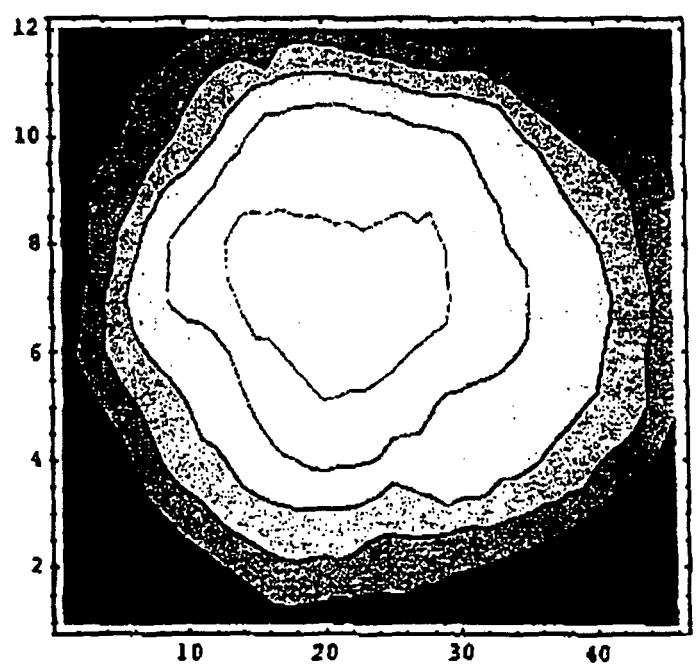

Pellets with the batch designation SFD E 0572 were investigated. An electron micrograph of pellets of this kind is shown in FIG. 11. A segment from the surface of a pellet from this batch was scanned with a laser profilometer, as described previously. A graphical representation of the measurement results is shown in FIG. 12A as a surface graph and in FIG. 12B as a contour diagram. The roughness was calculated using a reduced data set, as described previously. A surface graph based on the reduced data set is shown in FIG. 12C, and the corresponding contour diagram is shown in FIG. 12D.

Figure 12E:
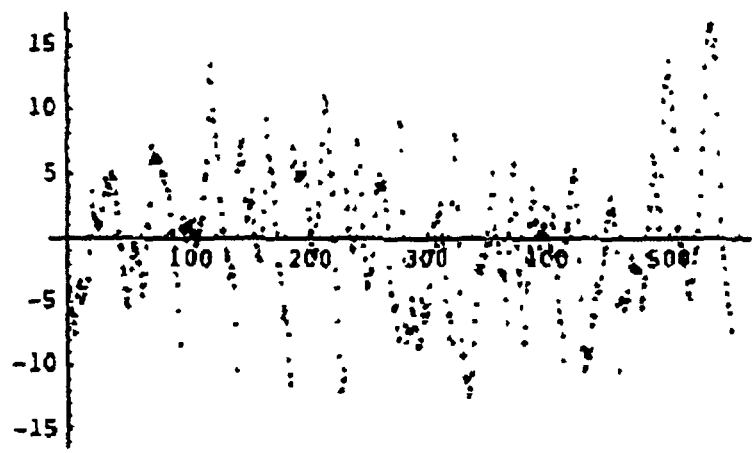

Using the method of least squares, a sphere was determined that provides an optimum representation of the measurement points of the reduced set. The coordinates of the center of this sphere were determined as 349 µm; 315 µm and −369 µm. The optimum radius R was 595 µm. The distribution of the data after adjustment is shown in FIG. 12E. Statistical analysis of the data shows that the mean roughness ad has a value of 5.5 µm and the relative mean roughness $\sigma_d/R$ has a value of 0.92%. The absolute roughness has a value of 17 µm. The pellet core investigated therefore fulfills the criteria according to the invention for a pellet core with a smooth surface.

Test Example 6

Figure 14A:
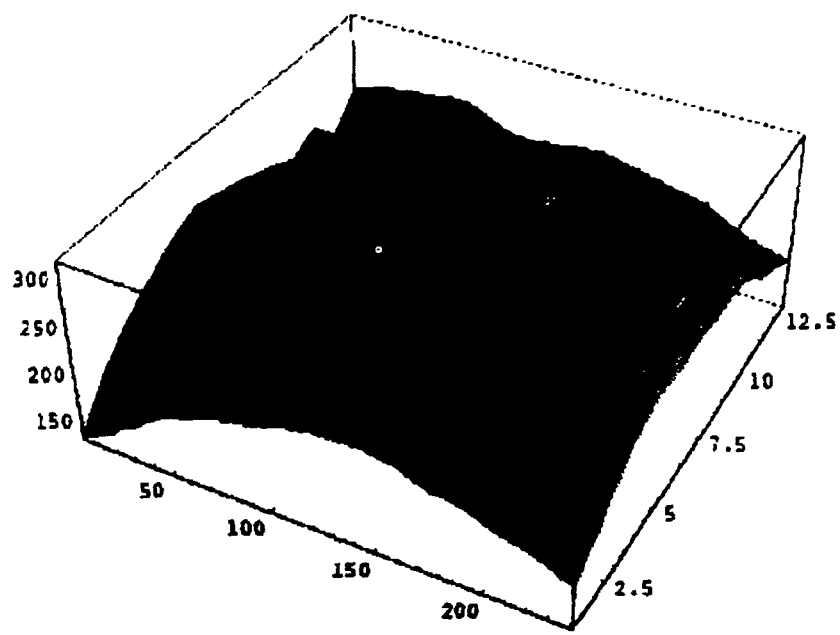
Figure 14B:
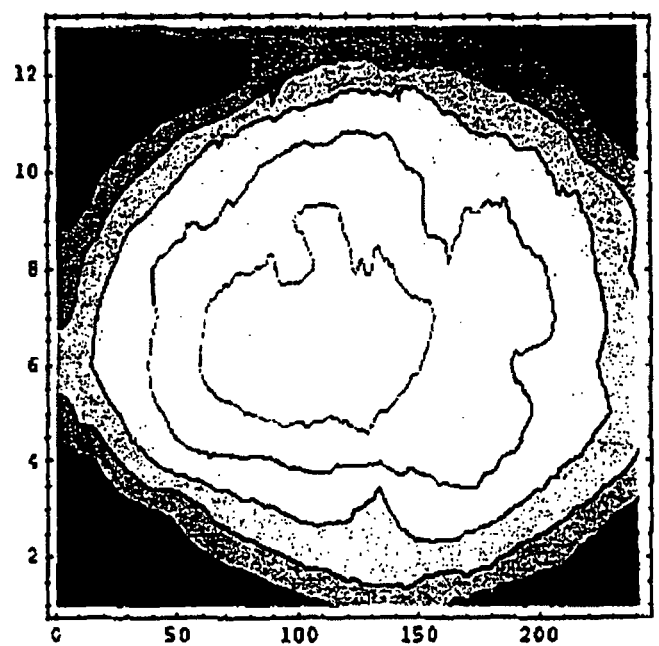
Figure 14C:
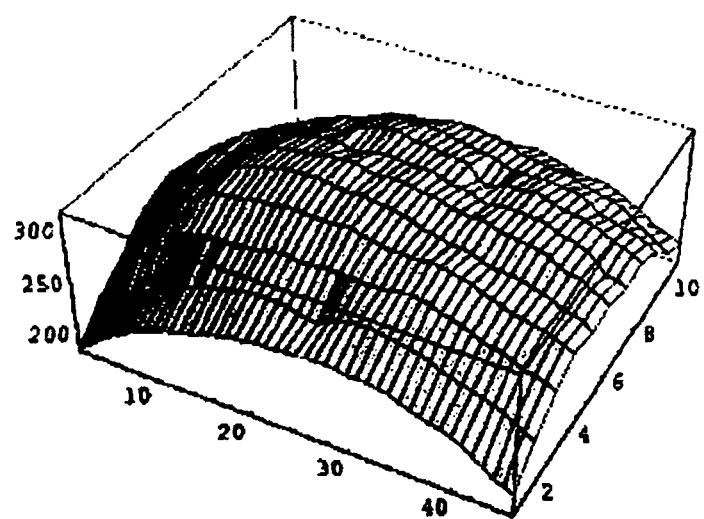
Figure 14D:
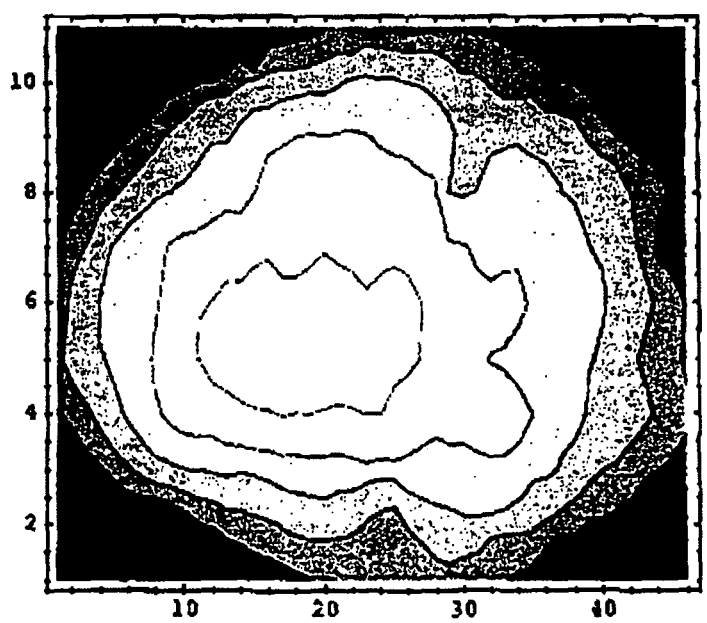

Pellets with the batch designation SFD E 0614 were investigated. An electron micrograph of pellets of this kind is shown in FIG. 13. A segment from the surface of a pellet from this batch was scanned with a laser profilometer, as described previously. A graphical representation of the measurement results is shown in FIG. 14A as a surface graph and in FIG. 14B as a contour diagram. The roughness was calculated using a reduced data set, as described previously. A surface graph based on the reduced data set is shown in FIG. 14C, and the corresponding contour diagram is shown in FIG. 14D.

Figure 14E:
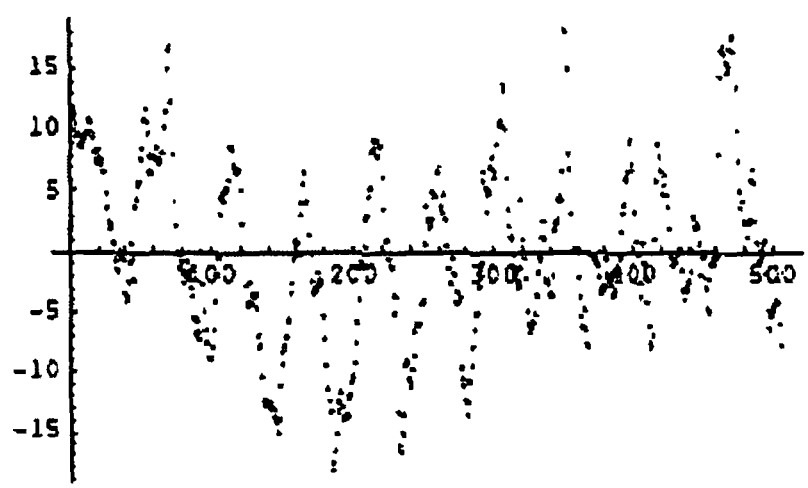

Using the method of least squares, a sphere was determined that provides an optimum representation of the measurement points of the reduced set. The coordinates of the center of this sphere were determined as 293 µm; 919 µm and −358 µm. The optimum radius R was 677 µm. The distribution of the data after adjustment is shown in FIG. 14E. Statistical analysis of the data shows that the mean roughness $\sigma_d$ has a value of 7.1 µm and the relative mean roughness $\sigma_d/R$ has a value of 1.06%. The absolute roughness has a value of 19 µm. The pellet core investigated therefore fulfills the criteria according to the invention for a pellet core with a smooth surface.

Test Example 7

Figure 15A:
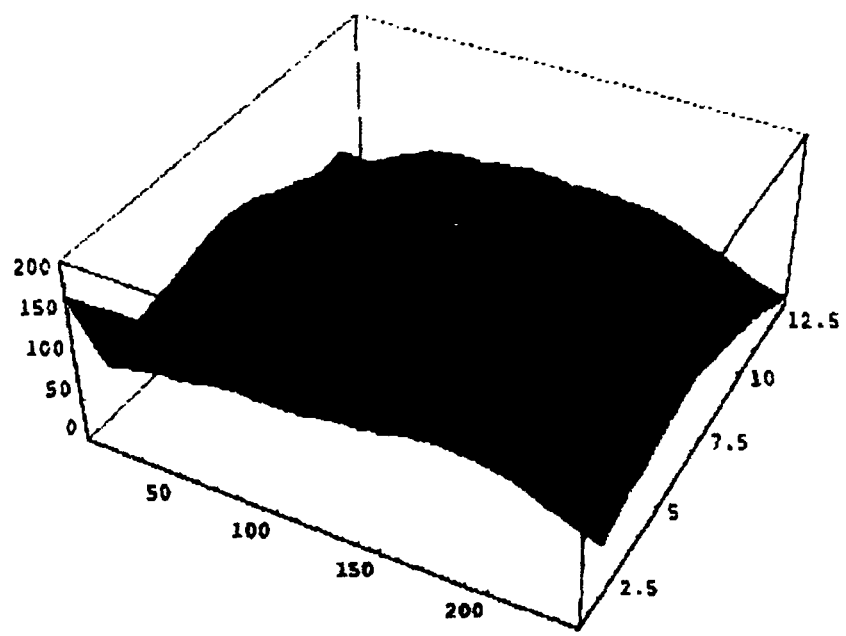
Figure 15B:
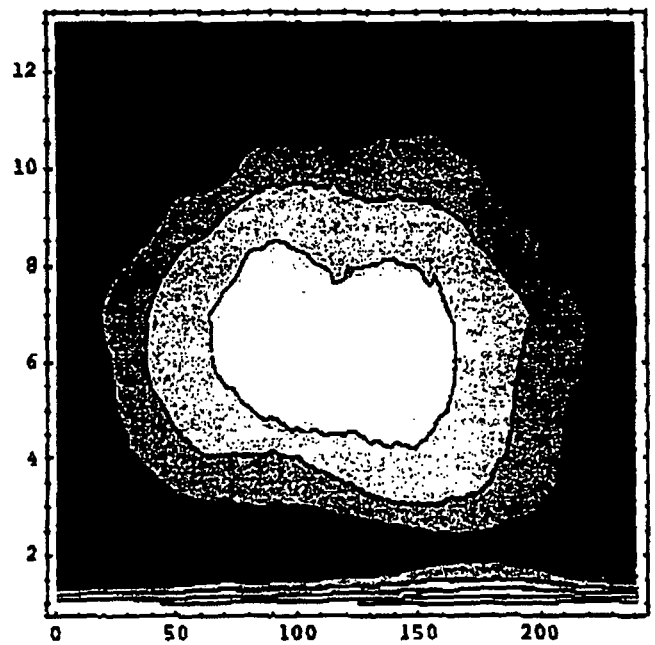
Figure 15C:
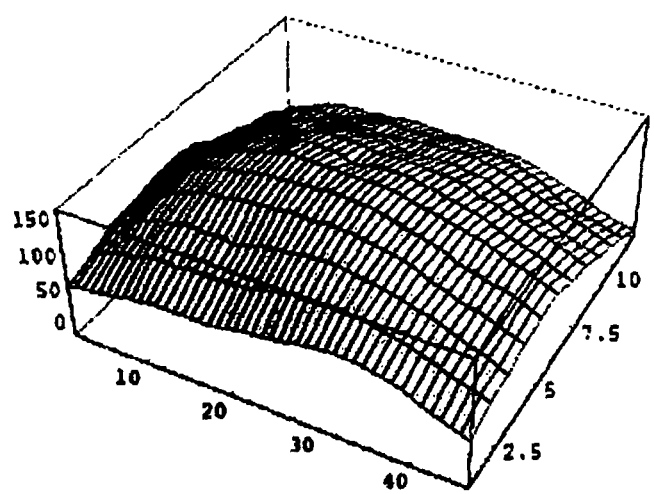
Figure 15D:
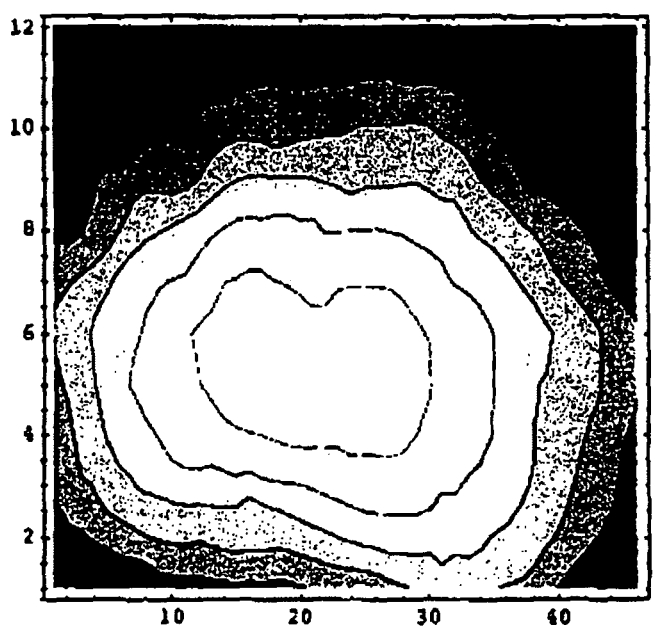

Another pellet from the same batch already mentioned in test example 6 was investigated in the same way as described previously. A graphical representation of the measurement results is shown in FIG. 15A as a surface graph and in FIG. 15B as a contour diagram. The reduced data set that was used for calculating the roughness forms the basis of the surface graph shown in FIG. 15C, and of the contour diagram shown in FIG. 15D.

Figure 15E:
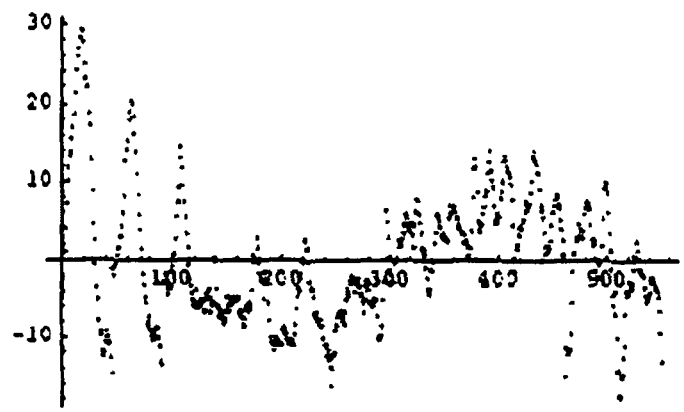

Using the method of least squares, a sphere was determined that provides an optimum representation of the measurement points of the reduced set. The coordinates of the center of this sphere were determined as 272 µm; 200 µm and −491 µm. The optimum radius R was 652 µm. The distribution of the data after adjustment is shown in FIG. 15E. Statistical analysis of the data shows that the mean roughness ad has a value of 8.2 µm and the relative mean roughness $\sigma_d/R$ has a value of 1.26%. The absolute roughness has a value of 30 µm. The pellet core investigated therefore fulfills the criteria according to the invention for a pellet core with a smooth surface.

The invention claimed is:

1. A pharmaceutical pellet, comprising:
   a spherical core having a smooth surface, and comprising:
      a core seed free of metoprolol salt, and comprising at least one carbohydrate; and
      a layer, comprising a metoprolol salt as an active substance, formed on top of the core seed; and
   a coating, comprising polyvinyl acetate, which is formed on the spherical core in an amount of 40-60 wt. % based on the weight of the spherical core, and which controls pH-independent release of the active substance.

2. The pellet according to claim 1;
   wherein the spherical core has a length-width ratio of less than 1.4.

3. The pellet according to claim 1;
   wherein the spherical core has a diameter in the range from 0.2 to 2 mm.

4. The pellet according to claim 1;
   wherein the spherical core has a mean roughness of less than 10 µm.

5. The pellet according to claim 1;
   wherein the spherical core has a relative mean roughness of less than 2%.

6. The pellet according to claim 1, further comprising:
   a protective outer coating which comprises a water-soluble film-forming agent.

7. The pellet according to claim 1, further comprising:
   an interlayer, comprising a water-soluble film-forming agent, arranged between the active-substance-containing layer of the spherical core the coating that controls the release of the active substance.

8. The pellet according to claim 1;
   wherein the at least one carbohydrate of the core seed is selected from the group consisting of sugar and microcrystalline cellulose.

9. The pellet according to claim 1;
   wherein the layer of the spherical core comprises 50% or more of the active substance.

10. The pellet according claim 1;
    wherein the release of the active substance follows a profile with a lag-phase of from 60 minutes to 840 minutes, such that, during the lag-phase, 5 wt % or less of the active substance is released.

11. The pellet according to claim 1;
wherein, after a lag-phase, at least 80 wt. % of the active substance still remaining in the pellet is released within 1,140 minutes.

12. The pellet according to claim 1;
wherein the active substance is released from the pellet with a profile such that, after a lag-phase, a release rate of the active substance is between 3 and 25 wt % per hour.

13. A collection of pellets, wherein at least 90% of the pellets correspond to the definition according to claim 1.

14. The collection as claimed in claim 13;
wherein the pellets have a particle size distribution such that 90% of the pellets have a diameter that differs from the mean diameter of all the pellets by not more than half the mean diameter.

15. A collection of cores, wherein at least 90% of the cores are spherical cores having a smooth surface and a length-width ratio of less than 1.4, and comprising:
  a core seed free of active substance, and comprising at least one carbohydrate; and
  a layer, comprising a metoprolol salt as an active substance, formed on top of the core seed.

16. A method for the production of a pellet as claimed in claim 1 wherein the method comprises the following steps:
  (a) providing the spherical core containing the active substance and having a length-width ratio of less than 1.4, where the spherical core also has a mean roughness of less than 10 μm and/or a relative mean roughness of less than 2%; and
  (b) spraying, on the spherical core, an aqueous solution or dispersion containing a film-forming agent that controls the pH-independent release of the active substance.

17. A method for the production of a tablet, comprising the following stages:
  (a) forming a mixture by mixing the pellets according to claim 1 with one or more ingredients selected front the group consisting of fillers, binders, disintegrants, flow regulators, and lubricants; and
  (b) forming a tablet by compressing the mixture.

18. The method as claimed in claim 17;
wherein the compression step, a portion of the pellets are disrupted so that the release of the active substance from the tablet has a lag-phase that is shorter than a lag-phase of the pellets.

19. A table which is produced according to the method as claimed in claim 17.

20. The tablet according to claim 19;
wherein the tablet ensures a constant release of the active substance within 24 hours.

21. The pellet according to claim 1;
wherein the metoprolol salt is metoprolol succinate.

\* \* \* \* \*